(12) United States Patent
Hunt et al.

(10) Patent No.: US 7,226,906 B2
(45) Date of Patent: Jun. 5, 2007

(54) CYCLOSPORIN ANALOGS FOR THE TREATMENT OF IMMUNOREGULATORY DISORDERS AND RESPIRATORY DISEASES

(75) Inventors: Kevin W. Hunt, Longmont, CO (US); Laurence E. Burgess, Boulder, CO (US)

(73) Assignee: Array BioPharma, Inc., Boulder, CO (US)

( * ) Notice: Subject to any disclaimer, the term of this patent is extended or adjusted under 35 U.S.C. 154(b) by 0 days.

(21) Appl. No.: 11/201,478

(22) Filed: Aug. 11, 2005

(65) Prior Publication Data

US 2006/0035822 A1    Feb. 16, 2006

Related U.S. Application Data

(63) Continuation-in-part of application No. 10/918,917, filed on Aug. 16, 2004.

(51) Int. Cl.
*A61K 38/13*    (2006.01)
*C07K 5/12*     (2006.01)
*C07K 7/64*     (2006.01)

(52) U.S. Cl. .......................... 514/11; 530/317; 530/321
(58) Field of Classification Search ...................... None
See application file for complete search history.

(56) References Cited

U.S. PATENT DOCUMENTS 5,256,547 A    10/1993    Rudat et al.
5,856,141 A    1/1999    Kim et al.
2002/0142946 A1    10/2002    Or et al.
2003/0087813 A1    5/2003    Or et al.
2003/0104992 A1    6/2003    Or et al.
2003/0109425 A1    6/2003    Or et al.
2003/0109426 A1    6/2003    Or et al.
2003/0166515 A1    9/2003    Or et al.
2003/0186855 A1    10/2003    Or et al.
2004/0110666 A1    6/2004    Or et al.

FOREIGN PATENT DOCUMENTS

WO    WO 03/030834 A2    4/2003
WO    WO 03/033010 A1    4/2003

OTHER PUBLICATIONS

S.R. Vippagunta, et al. Adv. Drug Delivery Rev. (2001) 48, pp. 3-26.*
Vickers, et al. "Human and Rate Lung Biotransformation of Cyclosporin A and its Derivatives Using Slices and Bronchial Epithelial Cells"; Drug Metabolism and Disposition; pp. 873-880; 1997; vol. 25, No. 7; US.
Tsvetelina, et al. "Synthesis and Biological Evaluation of Novel Cyclosporin A Analogues: Potential Soft Drugs for the Treatment of Autoimmune Diseases"; Journal of Medicinal Chemistry, American Chemical Society; pp. 674-676; Jan. 29, 2003; vol. 46, No. 5.

* cited by examiner

*Primary Examiner*—Cecilia J. Tsang
*Assistant Examiner*—Andrew D. Kosar
(74) *Attorney, Agent, or Firm*—John R Moore

(57) ABSTRACT

Provided are novel cyclosporin analogs, methods for their production, and their use for treating immunoregulatory and respiratory diseases, disorders, and conditions.

26 Claims, 8 Drawing Sheets

CYCLOSPORIN ANALOGS FOR THE TREATMENT OF IMMUNOREGULATORY DISORDERS AND RESPIRATORY DISEASES

CROSS-REFERENCE TO RELATED APPLICATIONS

This application is a continuation-in-part application of U.S. patent application Ser. No. 10/918,917, filed Aug. 16, 2004, which is incorporated herein by reference in its entirety.

BACKGROUND OF THE INVENTION

1. Field of the Invention

This invention relates to novel cyclosporin analogs, methods for their production, and their use for treating immunoregulatory and respiratory diseases, disorders, and conditions.

2. Description of the State of the Art

Cyclosporin, originally called cyclosporin A, is the main component of a large family of cyclic undecapeptides. This family, originally isolated from cultures of *Cylindrocarpon lucidum Booth* and *Tolypocladium Gams*, is produced as secondary fungal metabolites. Cyclosporin, initially pursued for its antifungal activities, is an effective immunosuppressant, acting primarily through T-lymphocytes via inhibition of the phosphatase calcineurin. Cyclosporin reduces the production of a range of cytokines, inhibiting the activation of various cell types, including those involved in cell-mediated immunity. Due to these properties, cyclosporin remains a first line therapy in the transplantation field.

Cyclosporin has the following structure:

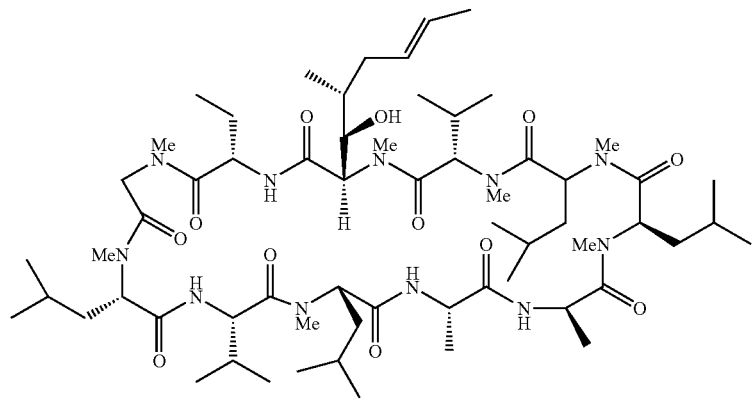

Cyclosporin A which can also be represented by the following structure showing the amino acid residues referred to by abbreviations in accordance with conventional practice:

```
┌──MeBmt-αAbu-Sar-MeLeu-Val-MeLeu-Ala-DAla-MeLeu-MeLeu-MeVal──┐
│      1    2    3     4     5     6    7     8     9    10   11     │
```

In addition to its wide use for preventing and treating organ transplant rejection, cyclosporin has been evaluated in a large range of disorders linked to immunoregulatory dysfunction and respiratory diseases. Cyclosporin, along with other calcineurin inhibitors, has been used for the treatment of nephritic syndrome, active Crohn's disease, acute ocular Behget syndrome, endogenous uveitis, psoriasis, atopic dermatitis, rheumatoid arthritis, aplastic anemia, primary biliary cirrhosis, celiac disease and other immunoregulatory diseases. Limited evidence suggests cyclosporin is effective in patients with intractable pyoderma gangrenosum, polymyostitis/dermatomyositis or severe, corticosteroid-dependent asthma (D. Faulds, K. L. Goa, and P. Benfield; *Drug Evaluation*, 1993, 45:953 and P. J. Wahab, et al., *Aliment Pharmacol. Ther.*, 2000, 14:767). The effect of cyclosporin and other calcineurin inhibitors on inflammatory cells and their mediators make it a promising therapy for asthma, COPD (chronic obstructive pulmonary disease), idiopathic pulmonary fibrosis, and other lung diseases. Treatment of these disorders with cyclosporin is limited to patients with severe disease that are either refractory or hypersensitive to standard treatments due to adverse events including, but not limited to, hypertrichosis, gingival hyperplasia, neurological effects, gastrointestinal effects, and renal dysfunction. Chronic cyclosporin treatment requires frequent renal function monitoring due to increased incidence of kidney failure.

The mechanism of toxicity of calcineurin inhibitors such as cyclosporin has been related to the mechanism of immunosuppression (F. J. Dumont, et al., *J. Exp. Med.*, 1992, 176:751–760). This strong link between cyclosporin's mechanism of action and many cyclosporin-induced toxicities has presented a significant challenge to medicinal chemists who have tried to improve the therapeutic index of cyclosporin through chemical modification. Indeed, these efforts, to date, have failed to separate cyclosporin efficacy from its toxicity. Segregation of efficacy and toxicity of cyclosporin analogs might still be possible by altering a compound's distribution or metabolism (N. H. Signal, et. al., *J. Exp. Med.*, 1991, 173:619). The systemic toxicity of cyclosporin A therefore limits its use for the treatment of certain diseases. It is therefore desirable to find compounds for the treatment of immunoregulatory and respiratory diseases with improved systemic efficacy and safety.

SUMMARY OF THE INVENTION

This invention provides novel cyclosporin analogs, methods to produce these compounds, and pharmaceutical compositions containing them for treating immunoregulatory and respiratory diseases, disorders, and conditions.

More particularly, the present invention provides cyclosporin analogs having the general Formula I

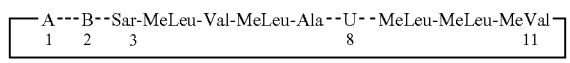

or a metabolite, solvate, resolved enantiomer, diastereomer, racemic mixture or pharmaceutically acceptable salt thereof, wherein:

residue A has the formula

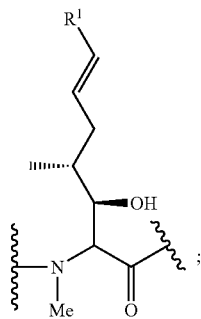

$R^1$ is alkyl, $Z_n$-Cycloalkyl, $Z_n$-heterocycloalkyl, —O-$Z_n$-OC(=O)alkyl, Zn—S-cycloalkyl, Zn—S-heterocycloalkyl, Zn—S—$Z_n R^5$, —C(=O)$NR_2 R^5$, —(CH=CH)A', or —C(=O)O-alkyl, wherein said alkyl is optionally substituted with one or more groups independently selected from cycloalkyl, aryl, oxo, S-heterocycle, OC(=O)-alkyl, $OA^r$ and

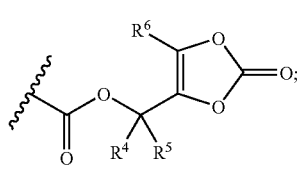

or $R^1$ is

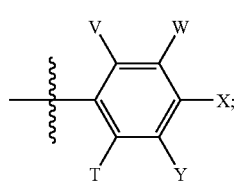

V, W, X, Y and T are independently selected from H, F, Br, Cl, alkyl, $Z_n$-Cycloalkyl, $Z_n$-heterocycloalkyl, $Z_n$-SH, $Z_n$-S-alkyl, $Z_n$-S-heterocycloalkyl, $Z_n$-$SA^r$, $Z_n$-S-$Z_n R^5$, —O-$Z_n$-heterocycloalkyl, O-$Z_n$-$R^5$, $Z_n$-OH, $Z_n$-O-alkyl, $Z_n$-O-heterocycloalkyl, $Z_n$-$OA^r$, $Z_n$-$NR^2 R^3$, $Z_n$-CN, and —O—CH$R^yC$(=O)$OR^x$, wherein said alkyl, cycloalkyl, heterocycloalkyl and $A^r$ portions are optionally substituted with one or more groups independently selected from oxo (provided it is not on said $A^r$), alkyl, F, Cl, Br, O-alkyl, $OA^r$ and $Z_n C$(=O)alkyl, provided that at least one of V, W, X, Y and T is other than hydrogen, and further provided that when W is F, Br or Cl, then X is other than H, and when X is F, Br or Cl, then W is other than H, or X is selected from

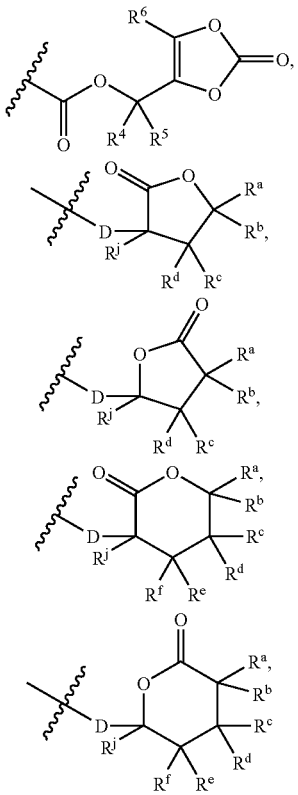

and the ring-opened forms thereof, wherein said ring-opened forms are derived from cleavage of the bond between the oxygen and carbonyl carbon;

or X and Y together with the atoms to which they are attached form a heterocyclic ring having one or more heteroatoms independently selected from N, O or S, wherein said heterocyclic ring is optionally substituted with one or more groups independently selected from oxo, alkyl, SH, and S-alkyl;

D is O, S, —CH$_2$—, —CH$_2$O—, —CH$_2$S—, or —CH$_2$CH$_2$—;

$R^a$, $R^b$, $R^c$, $R^d$, $R^e$, and $R^f$ are independently H, F, Br, Cl, alkyl, $Z_n$-O-alkyl, or $Z_n$-$OA^r$;

$R^j$ is H or alkyl;

$R^x$ is H, alkyl or CH$_2 A^r$;

$R^y$ is H, alkyl or $A^r$;

$A^r$ is a fully unsaturated, a partially unsaturated, or fully saturated carbocyclic or heterocyclic ring, wherein said carbocyclic and heterocyclic rings are optionally substituted with one or more groups independently selected from F, Cl, Br, I, CN, $CF_3$, $CHF_2$, $CH_2F$, OH, O-alkyl, alkoxyaryl, —OC(=O)$R^7$, C(=O)O$R^7$ and —SC(=O)$R^7$;

Z is alkylene having from 1 to 4 carbons, or alkenylene or alkynylene each having from 2 to 4 carbons, wherein said alkylene, alkenylene, and alkynylene are optionally substituted with one or more groups independently selected from alkyl, OH, O-alkyl, $NR^7R^8$ and alkyl-$NR^7R^8$;

$R^2$ and $R^3$ are independently H, alkyl, $Z_n$-$A^r$, or $Z_n$-O-alkyl, wherein said alkyl and $A^r$ portions are optionally substituted with one or more groups independently selected from F, Cl, Br and I;

$R^4$, $R^5$ and $R^6$ are independently H, $C_1$-$C_7$ alkyl, alkoxyalkyl, —$CO_2H$ or —C(=O)Oalkyl;

$R^7$ and $R^8$ are independently H, alkyl, alkenyl, or alkynyl;

residue B is -αABu-, -Val-, -Thr-, or NVa-;

residue U is -(D)Ala-, (-D)Ser-, —[O-(2-hydroxyethyl) (D)Ser]-, —[O-acyl(D)Ser] or —[O-(2-acyloxyethyl)(D) Ser]-; and n is 0, 1, 2, 3, or 4.

The compounds of the present invention have diminished plasma stability relative to known cyclosporin analogs. When administrated, the cyclosporins of the invention have potent efficacy at the site(s) of administration, while devoid of or exhibiting relatively reduced systemic activity. The cyclosporin analogs of the invention thus provide a means for the treatment of immunoregulatory and respiratory diseases, disorders, and conditions with the avoidance of unwanted systemic side effects.

The invention is also directed to pharmaceutically active metabolites and pharmaceutically acceptable salts of compounds of Formula I. Methods of making compounds of Formula I are also described.

The invention also relates to pharmaceutical compositions comprising a therapeutically effective amount of a compound of Formula I or a metabolite, solvate, resolved enantiomer, diastereomer, racemic mixture or pharmaceutically acceptable salt thereof.

The inventive compounds may be used advantageously in combination with other known therapeutic agents. Accordingly, this invention also relates to pharmaceutical compositions comprising a therapeutically effective amount of a compound of Formula I or a metabolite, solvate, resolved enantiomer, diastereomer, racemic mixture or pharmaceutically acceptable salt thereof, in combination with a second therapeutic agent.

In a further aspect the present invention provides a method of using the compounds of this invention as a medicament to treat immunoregulatory and respiratory diseases, disorders, and conditions. For example, this invention provides a method for treatment of a immunoregulatory or respiratory disorder in a mammal comprising administrating to said mammal one or more compounds of Formula I, or a metabolite, solvate, resolved enantiomer, diastereomer, racemic mixture or pharmaceutically acceptable salt thereof, in an amount effective to treat said disorder.

An additional aspect of the invention is the use of compounds of Formula I in the preparation of a medicament for the treatment or prevention of an immunoregulatory or respiratory disease, disorder or condition in a warm-blooded animal, for example, a mammal such as a human, suffering from such disorder. More particularly, the invention includes the use of a compound of Formula I, or a metabolite, solvate, resolved enantiomer, diastereomer, racemic mixture or pharmaceutically acceptable salt thereof, in the preparation of a medicament for the treatment or prevention of said disorder in a mammal.

In a further aspect the present invention provides a method of treating immunoregulatory and respiratory diseases, disorders, and conditions in a subject, which comprises administering to a warm-blooded animal a therapeutically effective amount of a compound of Formula I, or a metabolite, solvate, resolved enantiomer, diastereomer, racemic mixture or pharmaceutically acceptable salt thereof.

This invention further provides kits comprising one or more compounds of Formula I, or a metabolite, solvate, resolved enantiomer, diastereomer, racemic mixture or pharmaceutically acceptable salt thereof. The kit may further comprise a second compound or formulation comprising a second pharmaceutical agent for treating an immunoregulatory or respiratory disease, disorder, or condition.

Additional advantages and novel features of this invention shall be set forth in part in the description that follows, and in part will become apparent to those skilled in the art upon examination of the following specification or may be learned by the practice of the invention. The advantages of the invention may be realized and attained by means of the instrumentalities, combinations, compositions, and methods particularly pointed out in the appended claims.

BRIEF DESCRIPTION OF THE FIGURES

The accompanying drawings, which are incorporated herein and form a part of the specification, illustrate non-limiting embodiments of the present invention, and together with the description, serve to explain the principles of the invention.

In the Figures.

DETAILED DESCRIPTION OF THE INVENTION

Figure 1:
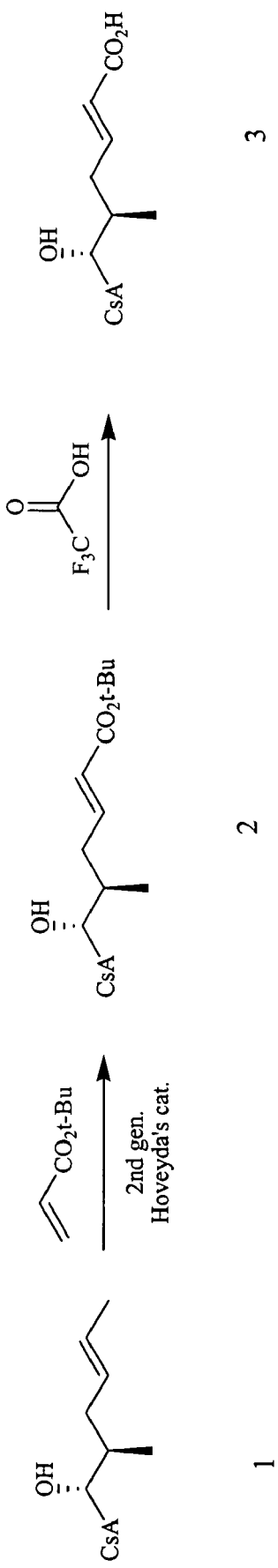
FIG. 1 shows a reaction scheme for the synthesis of compound 3.

The present invention provides cyclosporin analogs that are useful for treating immunoregulatory and respiratory diseases, disorders, and conditions. By provision of the cyclosporin analogs of the invention, which are topically active but systemically less active, the present invention provides cyclosporin therapy to subjects for whom such therapy might otherwise be excluded, for example, due to the risk of systemic side effects.

More specifically, present invention applies the "soft drug" concept to the preparation of cyclosporin analogs.

This approach limits the exposure of an active calcineurin inhibitor to organs (i.e., kidney) that are sensitive which results in toxicities, while maximizing the topical exposure of an active calcineurin inhibitor to diseased tissues and organs (e.g., skin, lung, gut, eye, etc.).

A "soft drug" is a compound that is a close structural analog of a known active drug that possesses a specific metabolic liability, and provides a predictable, controlled detoxification (N. Bodor, P. Buchwald, *Med. Res. Rev.*, 2000, 20:58). Most soft drugs are designed to act topically at the site of application and to be rendered inactive upon entering systemic circulation. Application of soft drug principles has allowed the launching of a number of drugs across several therapeutic areas. Investigations of other soft drugs continue in the area of antimicrobials, antichlolinergics, corticosteroids, β-blockers, immunoregulatory agents, analgesics, ACE inhibitors, antiarrhythmics, and others. For example, the soft drug concept has been applied to calcineurin inhibitors (T. Lazarova, et al., *J. Med. Chem.* 46:674 (2003) and T. H. Keller, et al., in *New Drugs for Asthma, Allergy and COPD*; Hansel, T. T., Barnes, P. J., Eds.; Progress in Respiratory Research, Vol. 31; Karger; Basel, Switzerland 2003; pp 237–240).

Applying the soft drug principles to cyclosporin analogs of the present invention allows the segregation of its efficacy in immunoregulatory disorders (lung, skin, eye, gut, nasal, colonic, ear, oral, vaginal diseases) from its use-limiting toxicity. A "soft" analog of the cyclosporin family is highly desirable, given the current lack of safe and efficacious treatment options for immunoregulatory disorders and severe lung diseases. Accordingly, the cyclosporin analogs of this invention include "soft" analogs of all naturally occurring cyclosporins, in addition to analogs accessible by total synthesis, fermentation, enzymatic catalysis, and/or genetic engineering.

In general, one aspect of the invention provides compounds of the general Formula I:

and metabolites, solvates, resolved enantiomers, diastereomers, racemic mixtures and pharmaceutically acceptable salts thereof, wherein:

residue A has the formula

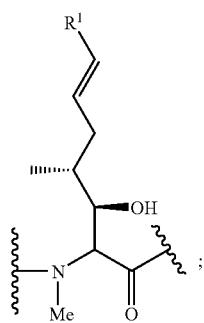

$R^1$ is alkyl, $Z_n$-Cycloalkyl, $Z_n$-heterocycloalkyl, —O-$Z_n$-OC(=O)alkyl, $Z_n$-S-cycloalkyl, $Z_n$-S-heterocycloalkyl, $Z_n$-S-$Z_n R^5$, —C(=O)NR$^2$R$^3$, —(CH=CH)A$^r$, or —C(=O)O-alkyl, wherein said alkyl is optionally substituted with one or more groups independently selected from cycloalkyl, aryl, oxo, S-heterocycle, OC(=O)-alkyl, OA$^r$ and

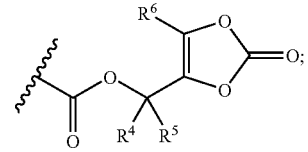

or $R^1$ is

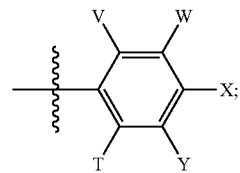

V, W, X, Y and T are independently selected from H, F, Br, Cl, alkyl, $Z_n$-Cycloalkyl, $Z_n$-heterocycloalkyl, $Z_n$-SH, $Z_n$-S-alkyl, $Z_n$-S-heterocycloalkyl, $Z_n$-SA$^r$, $Z_n$-S-$Z_n R^5$, —O-$Z_n$-heterocycloalkyl, O-$Z_n$-R$^5$, $Z_n$-OH, $Z_n$-O-alkyl, $Z_n$-O-heterocycloalkyl, $Z_n$-OA$^r$, $Z_n$-NR$^2$R$^3$, $Z_n$-CN, and —O—CHR$^y$C(=O)OR$^x$, wherein said alkyl, cycloalkyl, heterocycloalkyl and A portions are optionally substituted with one or more groups independently selected from oxo (provided it is not on said A), alkyl, F, Cl, Br, O-alkyl, A$^r$ and $Z_n$C(=O)alkyl, provided that at least one of V, W, X, Y and T is other than hydrogen, and further provided that when W is F, Br or Cl, then X is other than H, and when X is F, Br or Cl, then W is other than H, or X is selected from

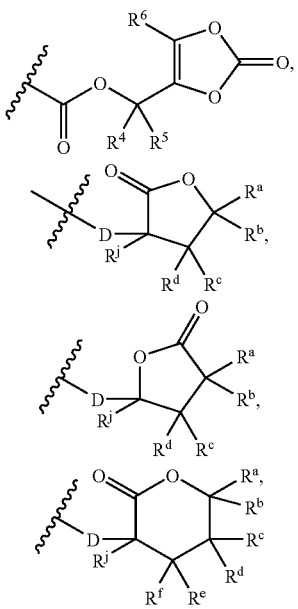

-continued

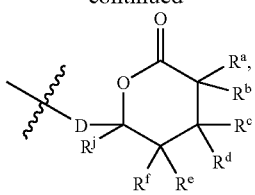

and the ring-opened forms thereof, wherein said ring-opened forms are derived from cleavage of the bond between the oxygen and carbonyl carbon;

or X and Y together with the atoms to which they are attached form a heterocyclic ring having one or more heteroatoms independently selected from N, O or S, wherein said heterocyclic ring is optionally substituted with one or more groups independently selected from oxo, alkyl, SH, and S-alkyl;

D is O, S, —CH$_2$—, —CH$_2$O—, —CH$_2$S—, or —CH$_2$CH$_2$—;

R$^a$, R$^b$, R$^c$, R$^d$, R$^e$, and R$^f$ are independently H, F, Br, Cl, alkyl, Z$_n$-O-alkyl, or Z$_n$-OA$^r$;

R$^1$ is H or alkyl;

R$^x$ is H, alkyl or CH$_2$A$^r$;

R$^y$ is H, alkyl or A$^r$;

A$^r$ is a fully unsaturated, a partially unsaturated, or fully saturated carbocyclic or heterocyclic ring, wherein said carbocyclic and heterocyclic rings are optionally substituted with one or more groups independently selected from F, Cl, Br, I, CN, CF$_3$, CHF$_2$, CH$_2$F, OH, O-alkyl, alkoxyaryl, —OC(=O)R$^7$, C(=O)OR$^7$ and —SC(=O)R$^7$;

Z is alkylene having from 1 to 4 carbons, or alkenylene or alkynylene each having from 2 to 4 carbons, wherein said alkylene, alkenylene, and alkynylene are optionally substituted with one or more groups independently selected from alkyl, OH, O-alkyl, NR$^7$R$^8$, and alkyl-NR$^7$R$^8$;

R$^2$ and R$^3$ are independently H, alkyl, Z$_n$-Ar, or Z$_n$-O-alkyl, wherein said alkyl and Ar portions are optionally substituted with one or more groups independently selected from F, Cl, Br and I;

R$^4$, R$^5$ and R$^6$ are independently H, C$_1$–C$_7$ alkyl, alkoxyalkyl, —CO$_2$H or —C(=O)Oalkyl;

R$^7$ and R$^8$ are independently H, alkyl, alkenyl, or alkynyl;

residue B is -αABu-, -Val-, -Thr-, or NVa-;

residue U is -(D)Ala-, (-D)Ser-, —[O-(2-hydroxyethyl)(D)Ser]-, —[O-acyl(D)Ser] or —[O-(2-acyloxyethyl)(D)Ser]-; and n is 0, 1, 2, 3, or 4.

In Formula I, the amino acid residues are referred to by abbreviations, e.g., -Ala-, -MeLeu-, -αAbu-, etc., in accordance with conventional practice, and are to be understood as having the L-configuration unless otherwise indicated. For example, the amino acid residue Ala is understood to have the L-configuration, whereas -(D)Ala- represents a residue having the D-configuration. Residue abbreviations preceded by "Me", as in the case of "MeLeu", represent α-N-methylated residues. Individual residues of the cyclosporin molecule of Formula I are numbered, as in the art, clockwise and starting with the residue -MeBmt- corresponding to residue 1. The same numerical sequence is employed throughout the specifications and claims.

In one embodiment of said compound of Formula I, residue B is -αAbu- and residue U is -(D)Ala-.

As stated above, in one embodiment of Formula I, or X is selected from

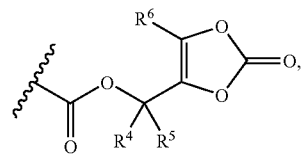

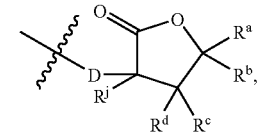

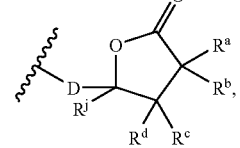

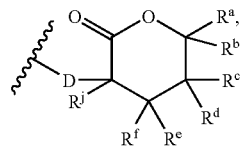

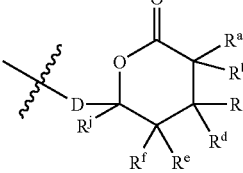

and the ring-opened forms thereof. The ring-opened forms of X arise from cleavage of the oxygen and carbonyl carbon ring atoms and include, but are not limited to:

Ring form            Ring-opened form

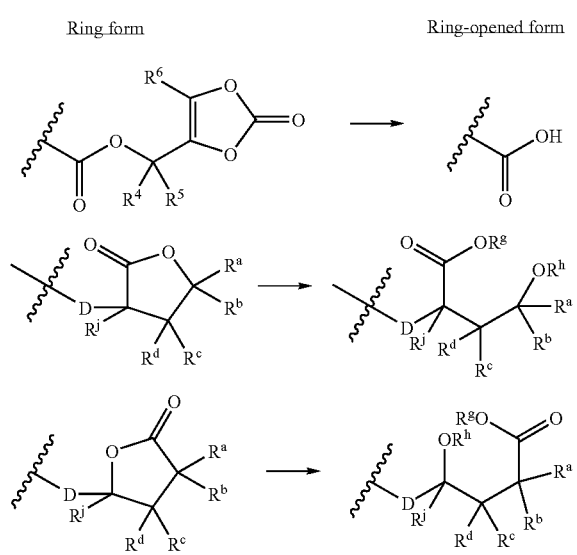

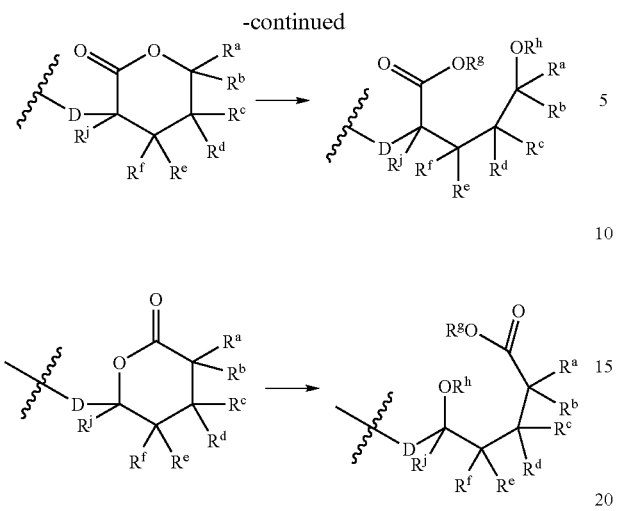

wherein $R^g$ and $R^h$ are independently selected from H, alkyl, $Z_n$-O-alkyl, $Z_n$-OA$^r$, C(=O)alkyl and C(=O)H.

In certain embodiments of compounds of Formula I, $R^1$ is

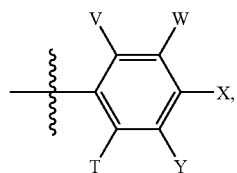

wherein V, W, X, Y and T are as defined herein. In one embodiment, X and W are independently H, Br, Cl or —OA$^r$. In a particular embodiment, $R^1$ is

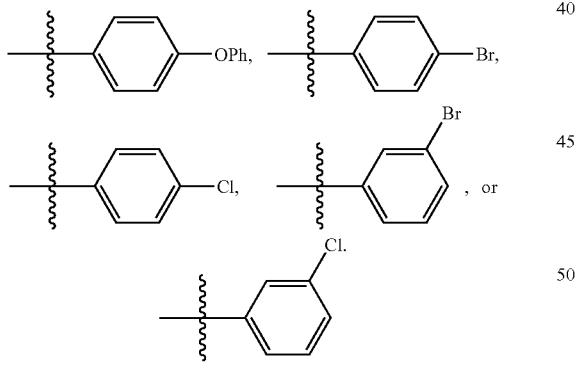

In another embodiment, $R^1$ is

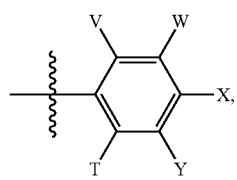

wherein X is selected from

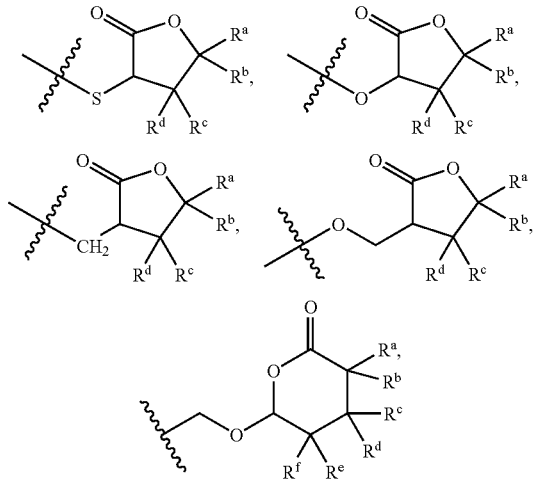

and V, W, Y, T, $R^a$, $R^b$, $R^c$, $R^d$, $R^e$ and $R^f$ are as defined herein.

In certain embodiments, $R^a$ and $R^b$ are independently H or alkyl. In particular embodiments, $R^1$ is

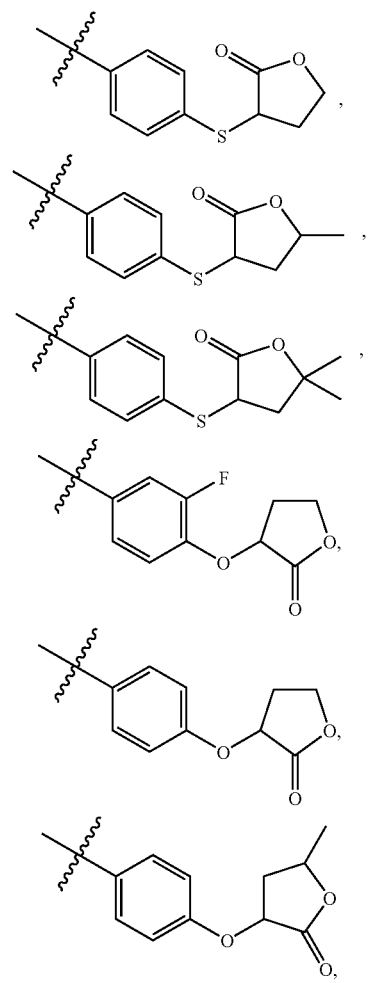

-continued

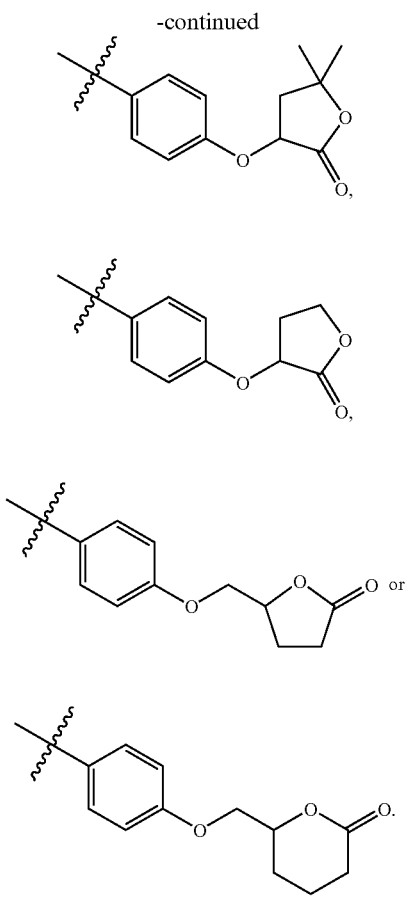

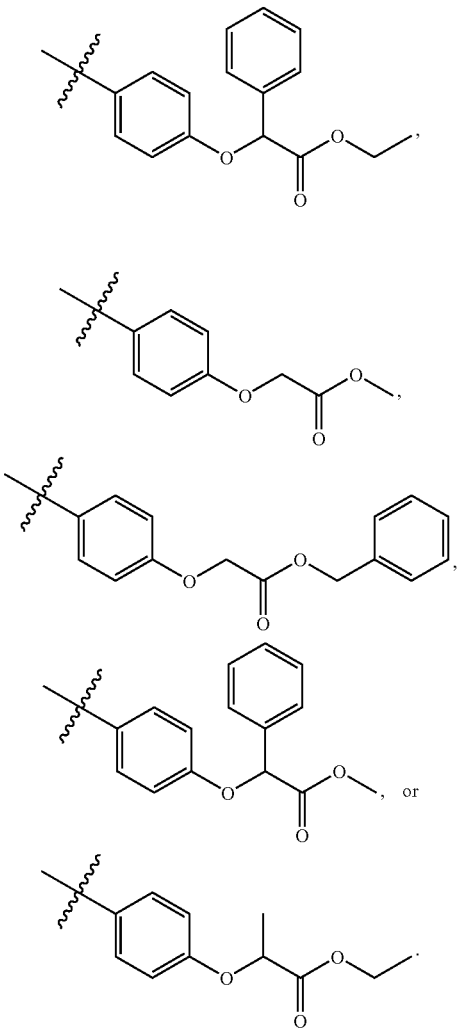

In yet another embodiment of compounds of Formula I, $R^1$ is

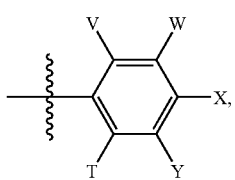

wherein X is alkyl and V, W, Y and T are as defined herein. In certain embodiments, said alkyl is substituted with one or more groups independently selected from F, Cl, Br, and I. In a particular embodiment, X is $CH_2Cl$.

In yet another embodiment of compounds of Formula I, $R^1$ is

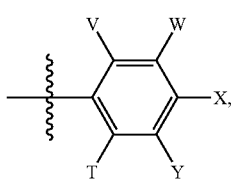

wherein X is $OCHR^yC(=O)OR^x$, and V, W, Y, T, $R^x$ and $R^y$ are as defined herein. In a particular embodiment, $R^1$ is In yet another embodiment of compounds of Formula I, $R^1$ is

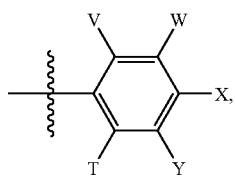

wherein X is $Z_n$-S-$Z_nR^5$, and V, W, Y, T, $R^5$, Z and n are as defined herein. In certain embodiments, $R^5$ is —C(=O)O-alkyl. In a particular embodiment, $R^1$ is

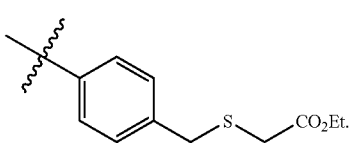

In yet another embodiment of compounds of Formula I, R¹ is

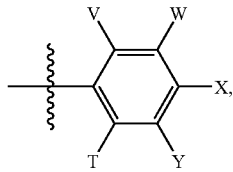

wherein X is O-$Z_n$-R⁵, and V, W, Y, T, R⁵, Z and n are as defined herein. In certain embodiments, R⁵ is $CO_2H$ or —C(=O)Oalkyl. In a particular embodiment, R¹ is

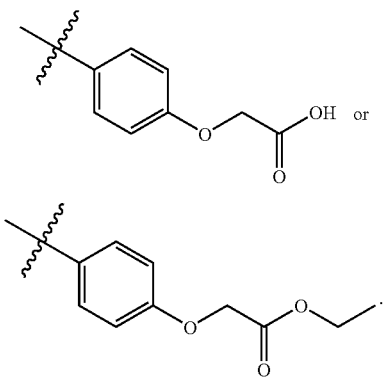

In yet another embodiment of compounds of Formula I, R¹ is

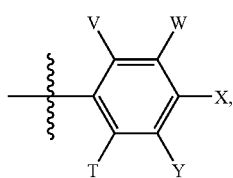

wherein X and W together with the atoms to which they are attached form a heterocyclic ring. In a particular embodiment, R¹ is

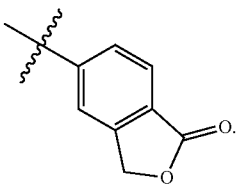

In yet another embodiment, R¹ is C(=O)O-alkyl. In certain embodiments, said alkyl is substituted with one or more groups independently selected from cycloalkyl, S-heterocycle, oxo, and OA$^r$. In a particular embodiment, R¹ is

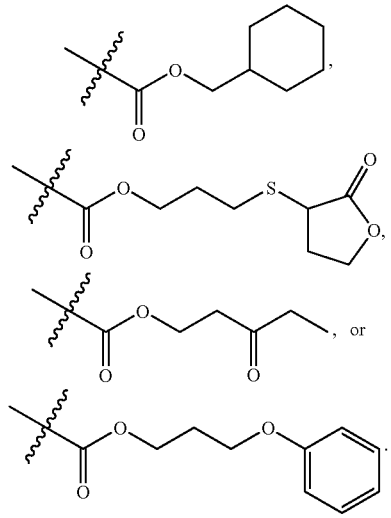

In yet another embodiment, R¹ is —C(=O)NR²R³, wherein R² and R³ are as defined herein. In certain embodiments, R² is H or alkyl. In certain embodiments, R³ is $Z_n$-A$^r$ or O-alkyl. In particular embodiments, R¹ is

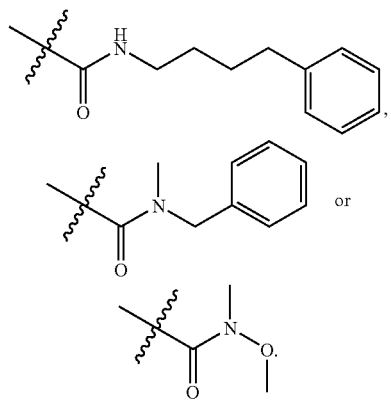

In yet another embodiment, R¹ is —O-$Z_n$-OC(=O)alkyl, wherein Z and n are as defined herein. In certain embodiments, R¹ is —OCH₂CH₂OC(=O)CH₃.

The term "alkyl" as used herein refers to a saturated linear or branched-chain monovalent hydrocarbon radical having one to ten carbon atoms, wherein the alkyl radical may be optionally substituted independently with one or more substituents described below. Examples of alkyl radicals include $C_1$–$C_{12}$ hydrocarbon moieties such as methyl(Me, —CH₃), ethyl(Et, —CH₂CH₃), 1-propyl(n-Pr, n-propyl, —CH₂CH₂CH₃), 2-propyl(i-Pr, i-propyl, —CH(CH₃)₂), 1-butyl (n-Bu, n-butyl, —CH₂CH₂CH₂CH₃), 2-methyl-1-propyl(i-Bu, i-butyl, —CH₂CH(CH₃)₂), 2-butyl(s-Bu, s-butyl, —CH(CH₃)CH₂CH₃), 2-methyl-2-propyl(t-Bu, t-butyl, —C(CH₃)₃), 1-pentyl(n-pentyl, —CH₂CH₂CH₂CH₂CH₃), 2-pentyl(—CH(CH₃)CH₂CH₂CH₃), 3-pentyl(—CH(CH₂CH₃)₂), 2-methyl-2-butyl(—C(CH₃)₂CH₂CH₃), 3-methyl-2-butyl(—CH(CH₃)CH(CH₃)₂), 3-methyl-1-butyl(—CH₂CH₂CH(CH₃)₂), 2-methyl-1-butyl(—CH₂CH(CH₃)CH₂CH₃), 1-hexyl(—CH₂CH₂CH₂CH₂CH₂CH₃), 2-methyl-2-pentyl(—CH(CH$_3$)CH$_2$CH$_2$CH$_3$), 3-hexyl (—CH(CH$_2$CH$_3$)(CH$_2$CH$_2$CH$_3$)), 2-methyl-2-pentyl(—C(CH$_3$)$_2$CH$_2$CH$_2$CH$_3$), 3-methyl-2-pentyl(—CH(CH$_3$)CH(CH$_3$)CH$_2$CH$_3$), 4-methyl-2-pentyl(—CH(CH$_3$)CH$_2$CH(CH$_3$)$_2$), 3-methyl-3-pentyl(—C(CH$_3$)(CH$_2$CH$_3$)$_2$), 2-methyl-3-pentyl(—CH(CH$_2$CH$_3$)CH(CH$_3$)$_2$), 2,3-dimethyl-2-butyl(—C(CH$_3$)$_2$CH(CH$_3$)$_2$), 3,3-dimethyl-2-butyl (—CH(CH$_3$)C(CH$_3$)$_3$, 1-heptyl, and 1-octyl.

The term "alkenyl" refers to a linear or branched-chain monovalent hydrocarbon radical having two to 10 carbon atoms and at least one double bond, and include, but is not limited to, ethenyl, propenyl, 1-but-3-enyl, 1-pent-3-enyl, 1-hex-5-enyl and the like, wherein the alkenyl radical may be optionally substituted independently with one or more substituents described herein, and includes radicals having "cis" and "trans" orientations, or alternatively, "E" and "Z" orientations. The term "alkenyl" includes allyl (RC═CHCHR).

The term "alkynyl" refers to a linear or branched monovalent hydrocarbon radical of two to twelve carbon atoms containing at least one triple bond. Examples include, but are not limited to, ethynyl, propynyl, butynyl, pentyn-2-yl and the like, wherein the alkynyl radical may be optionally substituted independently with one or more substituents described herein.

The term "alkylene" as used herein refers to a linear or branched saturated divalent hydrocarbon radical of one to twelve carbon atoms, e.g., methylene (—CH$_2$—), 1,2-ethylene(—CH$_2$CH$_2$—), 1,3-propylene(—CH$_2$CH$_2$CH$_2$—), 1,4-butyl(—CH$_2$CH$_2$CH$_2$CH$_2$—), and the like.

The term "alkenylene" refers to a linear or branched divalent hydrocarbon radical of two to twelve carbons containing at least one double bond, wherein the alkenylene radical may be optionally substituted independently with one or more substituents described herein. Examples include, but are not limited to, ethenylene (—CH═CH—), propenylene (—CH═CHCH$_2$—), and the like.

The term "alkynylene" refers to a linear or branched divalent hydrocarbon radical of two to twelve carbons containing at least one triple bond, wherein the alkynylene radical may be optionally substituted independently with one or more substituents described herein. Alkynylene radicals include, but are not limited to: acetylene (—C≡C—), propargyl (—CH$_2$C≡C—), and 4-pentynyl (—CH$_2$CH$_2$CH$_2$C≡C—).

The term "alkoxyalkyl" refers to a saturated linear or branched-chain monovalent hydrocarbon radical of one to twelve carbon atoms and substituted with one or more alkoxy groups.

The terms "carbocycle," "carbocyclyl," or "cycloalkyl" are used interchangeably herein and refer to saturated or partially unsaturated cyclic hydrocarbon radical having from three to twelve carbon atoms. The term "cycloalkyl" includes monocyclic and polycyclic (e.g., bicyclic and tricyclic) cycloalkyl structures, wherein the polycyclic structures optionally include a saturated or partially unsaturated cycloalkyl fused to a saturated or partially unsaturated cycloalkyl or heterocycloalkyl ring or an aryl or heteroaryl ring. Examples of cycloalkyl groups include, but are not limited to, cyclopropyl, cyclobutyl, cyclopentyl, cyclohexyl, cycloheptyl, and the like. Bicyclic carbocycles have 7 to 12 ring atoms, e.g. arranged as a bicyclo [4,5], [5,5], [5,6] or [6,6] system, or 9 or 10 ring atoms arranged as a bicyclo [5,6] or [6,6] system, or as bridged systems such as bicyclo [2.2.1]heptane, bicyclo[2.2.2]octane, and bicyclo[3.2.2] nonane. The cycloalkyl may be optionally substituted independently at one or more substitutable positions with one or more substituents described herein. Such cycloalkyl groups may be optionally substituted with, for example, one or more groups independently selected from C$_1$–C$_6$ alkyl, C$_1$–C$_6$ alkoxy, halogen, hydroxy, cyano, nitro, amino, mono (C$_1$–C$_6$)alkylamino, di(C$_1$–C$_6$)alkylamino, C$_2$–C$_6$ alkenyl, C$_2$–C$_6$ alkynyl, C$_1$–C$_6$ haloalkyl, C$_1$–C$_6$ haloalkoxy, amino (C$_{1-C6}$)alkyl, mono(C$_1$–C$_6$)alkylamino(C$_1$–C$_6$)alkyl and di(C$_1$–C$_6$)alkylamino(C$_1$–C$_6$)alkyl.

The terms "heterocycloalkyl," "heterocycle" and "heterocyclyl" are used interchangeably herein and refer to a saturated or partially unsaturated carbocyclic radical of 3 to 8 ring atoms in which at least one ring atom is a heteroatom selected from nitrogen, oxygen and sulfur, the remaining ring atoms being C, where one or more ring atoms may be optionally substituted independently with one or more substituents described below. The radical may be a carbon radical or heteroatom radical. The term "heterocycle" includes heterocycloalkoxy. The term further includes fused ring systems which include a heterocycle fused to an aromatic group. "Heterocycloalkyl" also includes radicals where heterocycle radicals are fused with aromatic or heteroaromatic rings. Examples of heterocycloalkyl rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo [4.1.0]heptanyl, azabicyclo[2.2.2]hexanyl, 3H-indolyl quinolizinyl and N-pyridyl ureas. Spiro moieties are also included within the scope of this definition. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). An example of a heterocyclic group wherein 2 ring carbon atoms are substituted with oxo (═O) moieties is 1,1-dioxo-thiomorpholinyl. The heterocycle groups herein are unsubstituted or, as specified, substituted in one or more substitutable positions with various groups. For example, such heterocycle groups may be optionally substituted with, for example, one or more groups independently selected from C$_1$–C$_6$ alkyl, C$_1$–C$_6$ alkoxy, halogen, hydroxy, cyano, nitro, amino, mono(C$_1$–C$_6$)alkylamino, di(C$_1$–C$_6$)alkylamino, C$_2$–C$_6$alkenyl, C$_2$–C$_6$alkynyl, C$_1$–C$_6$ haloalkyl, C$_{1-C6}$ haloalkoxy, amino (C$_1$–C$_6$)alkyl, mono(C$_1$–C$_6$)alkylamino(C$_1$–C$_6$)alkyl or di(C$_1$–C$_6$)alkylamino(C$_1$–C$_6$)alkyl.

The term "aryl" refers to a monovalent aromatic carbocyclic radical having a single ring (e.g., phenyl), multiple rings (e.g., biphenyl), or multiple condensed rings in which at least one is aromatic, (e.g., 1,2,3,4-tetrahydronaphthyl, naphthyl, etc.), which is optionally substituted with one or more substituents independently selected from, for example, halogen, lower alkyl, lower alkoxy, trifluoromethyl, aryl, heteroaryl and hydroxy.

The term "heteroaryl" refers to a monovalent aromatic radical of 5-, 6-, or 7-membered rings and includes fused ring systems (at least one of which is aromatic) of 5–10 atoms containing at least one and up to four heteroatoms selected from nitrogen, oxygen, and sulfur. Examples of heteroaryl groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Spiro moieties are also included within the scope of this definition. Heteroaryl groups are optionally substituted with one or more substituents independently selected from, for example, halogen, lower alkyl, lower alkoxy, haloalkyl, aryl, heteroaryl, and hydroxy.

In general, the various moieties or functional groups of the compounds of Formula I may be optionally substituted with one or more substituents. Examples of substituents suitable for purposes of this invention include, but are not limited to, oxo, halogen, cyano, nitro, trifluoromethyl, fluoromethoxy, difluoromethoxy, trifluoromethoxy, azido, —NR"SO$_2$R', —SO$_2$NR'R", —C(=O)R', —C(=O)OR', —OC(=O)R', —NR"C(=O)OR', —NR"C(=O)R', —C(=O)NRR'R", —NR'R", —NR'''C(=O)N'R", —NR'''C(NCN)NR'R", —OR', aryl, heteroaryl, arylalkyl, heteroarylalkyl, heterocyclyl, and heterocyclylalkyl, where R', R" and R''' are independently H, alkyl, heteroalkyl, cycloalkyl, heterocycloalkyl, alkenyl, alkynyl, aryl or heteroaryl.

The compounds of this invention may possess one or more asymmetric centers; such compounds can therefore be produced as individual (R)— or (S)-stereoisomers or as mixtures thereof. Unless indicated otherwise, the description or naming of a particular compound in the specification and claims is intended to include both individual enantiomers, diastereomers mixtures, racemic or otherwise, thereof. Accordingly, this invention also includes all such isomers, including diastereomeric mixtures, pure diastereomers and pure enantiomers of compound of Formula I. The term "enantiomer" refers to two stereoisomers of a compound which are non-superimposable mirror images of one another. The term "diastereomer" refers to a stereoisomer with two or more centers of chirality and whose molecules are not mirror images of one another. Diastereomers have different physical properties, e.g. melting points, boiling points, spectral properties, and reactivities.

Diastereomeric mixtures can be separated into their individual diastereomers on the basis of their physical chemical differences by methods known to those skilled in the art, for example, by chromatography or fractional crystallization. Enantiomers can be separated by converting the enantiomer mixture into a diastereomeric mixture by reaction with an appropriate optically active compound (e.g., alcohol), separating the diastereomers and converting (e.g., hydrolyzing) the individual diastereomers to the corresponding pure enantiomers. Enantiomers can also be separated by use of a chiral HPLC column. Methods for the determination of stereochemistry and the separation of stereoisomers are well known in the art (see discussion in Chapter 4 of "Advanced Organic Chemistry", 4th edition, J. March, John Wiley and Sons, New York, 1992).

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

A single stereoisomer, for example, an enantiomer substantially free of its stereoisomer, may be obtained by resolution of a racemic mixture using a method such as formation of diastereomers using optically active resolving agents (Eliel, E. and Wilen, S. *Stereochemistry of Organic Compounds*, John Wiley & Sons, Inc., New York, 1994; Lochmuller, C. H., (1975) *J. Chromatogr.*, 113(3):283–302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: *Drug Stereochemistry, Analytical Methods and Pharmacology*, Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (Wilen, S., "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g. (–) menthyl chloroformate in the presence of base, or Mosher ester, α-methoxy-α-(trifluoromethyl)phenyl acetate (Jacob III, (1982) *J. Org. Chem.* 47:4165), of the racemic mixture, and analyzing the NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase (*Chiral Liquid Chromatography* (1989) W. J. Lough, Ed., Chapman and Hall, New York; Okamoto, (1990) *J. of Chromatogr.* 513:375–378). Enriched or purified enantiomers can be distinguished by methods used to distinguish other chiral molecules with asymmetric carbon atoms, such as optical rotation and circular dichroism.

In addition to compounds of Formula I, the invention also includes solvates, pharmaceutically active metabolites, and pharmaceutically acceptable salts of such compounds.

The term "solvate" refers to an aggregate of a molecule with one or more solvent molecules.

A "pharmaceutically active metabolite" is a pharmacologically active product produced through metabolism in the body of a specified compound or salt thereof. Metabolites of a compound may be identified using routine techniques known in the art and their activities determined using tests such as those described herein. Active metabolites of a compound may be identified using routine techniques known in the art.

A "pharmaceutically acceptable salt," unless otherwise indicated, includes salts that retain the biological effectiveness of the free acids and bases of the specified compound and that are not biologically or otherwise undesirable. A compound of the invention may possess a sufficiently acidic, a sufficiently basic, or both functional groups, and accordingly react with any of a number of inorganic or organic bases, and inorganic and organic acids, to form a pharmaceutically acceptable salt. Examples of pharmaceutically acceptable salts include those salts prepared by reaction of the compounds of the present invention with a mineral or organic acid or an inorganic base, such salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyn-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methanesulfonates, propanesulfonates, naphthalene-1-sulfonates, naphthalene-2-sulfonates, and mandelates. Since a single compound of the present invention may include more than one acidic or basic moiety, the compounds of the present invention may include mono, di or tri-salts in a single compound.

If the inventive compound is a base, the desired pharmaceutically acceptable salt may be prepared by any suitable method available in the art, for example, treatment of the free base with an acidic compound, particularly an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid such as glucuronic acid or galacturonic acid, an alpha hydroxy acid such as citric acid or tartaric acid, an amino acid such as aspartic acid or glutamic acid, an aromatic acid such as benzoic acid or cinnamic acid, a sulfonic acid such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base. Examples of suitable inorganic salts include those formed with alkali and alkaline earth metals such as lithium, sodium, potassium, barium and calcium. Examples of suitable organic base salts include, for example, ammonium, dibenzylammonium, benzylammonium, 2-hydroxyethylammonium, bis(2-hydroxyethyl)ammonium, phenylethylbenzylamine, dibenzylethylenediamine, and the like salts. Other salts of acidic moieties may include, for example, those salts formed with procaine, quinine and N-methylglucosamine, plus salts formed with basic amino acids such as glycine, ornithine, histidine, phenylglycine, lysine and arginine.

The inventive compounds may be prepared using the reaction routes and synthesis schemes as described below, employing the techniques and reagents available in the art or can be synthesized according to the methods described in the Examples and FIGS. 1–8. The cyclosporin A or cyclosporin derivative used as the starting material for the reactions shown in FIGS. 1–8 includes, but is not limited to, a fermentation product or a synthetic product made by solution phase chemistry. A fermentation product may be made from highly productive strains such as, but not limited to, a *Sesquicillopsis rosariensis* G. ARNOLD F605; *Tolypocladium inflatum* wb6-5; Fusant, *Tolypocladium inflatum* KD461 (see, for example, U.S. Pat. Nos. 5,256,547 and 5,856,141). Alternatively, the starting material may be made by solution phase chemistry either by sequentially assembling amino acids or by linking suitable small peptide fragments, where the units are linked by, for example, amide, ester or hydroxylamine linkages (see, for example, Muller, *Methoden der organischen, Chemie* vol. XV/2, pp 1–364, Thieme Verlag, Stuttgart, 1974; Stewart, Young, Solid Phase Peptide Synthesis, pp 31 to 34, 71 to 82, Pierce Chemical Company, Rockford, 1984; Bodanszky, Kausner, Ondetti, Peptide Synthesis, pp 85 to 128, John Wiley & Sons, New York, 1976).

One method for the preparation of compounds of Formula I comprises reacting cyclosporin A or a cyclosporin derivative with an olefin having a terminal double bond using a catalyst such as 1,3-(bis(mesityl)-2-imidazolidinylidene)dichloro-(o-isopropoxyphenylmethylene)ruthenium (Hoveyda-Grubbs' catalyst, also known as Hoveyda's second generation catalyst; *Org. Biomol. Chem.*, 2004, 2:8–23), or any other suitable catalyst, such as Grubb's ruthenium alkylidine, Grubbs dihydroimidazole ruthenium, Shrock-Hoveyda molybdenum catalysts or benzylidine catalysts (U.S. Pat. No. 6,111,121; Reviews: *Synlett*, 1999, 2:267; Ivin, K. J., Mol, J. C., *Olefin Metathesis and Metathesis Polymerization*, $2^{nd}$ ed., Academic Press, New York, 1997; *J. Org. Chem.*, 2000, 65:2204–2207) or molybdenum catalysts (*J. Am. Chem. Soc.*, 1990, 112:3875; *J. Am. Chem. Soc.*, 1996, 118:10926–10927) in the presence of a lithium salt such as lithium bromide, lithium chloride, lithium trifluoroacetate, or a lithium triflate of a Lewis acid such as titanium isopropoxide in an organic solvent.

After the metathesis reaction, the reaction products can be further reacted to produce the compounds of the present invention. For example, FIG. 1 shows the reaction scheme for the synthesis of compound 2, obtained by the reaction between cyclosporin A and t-butyl acrylate catalyzed by Hoveyda's $2^{nd}$ generation catalyst. Compound 2 is then treated with trifluoroacetic acid to provide compound 3.

Figure 2:
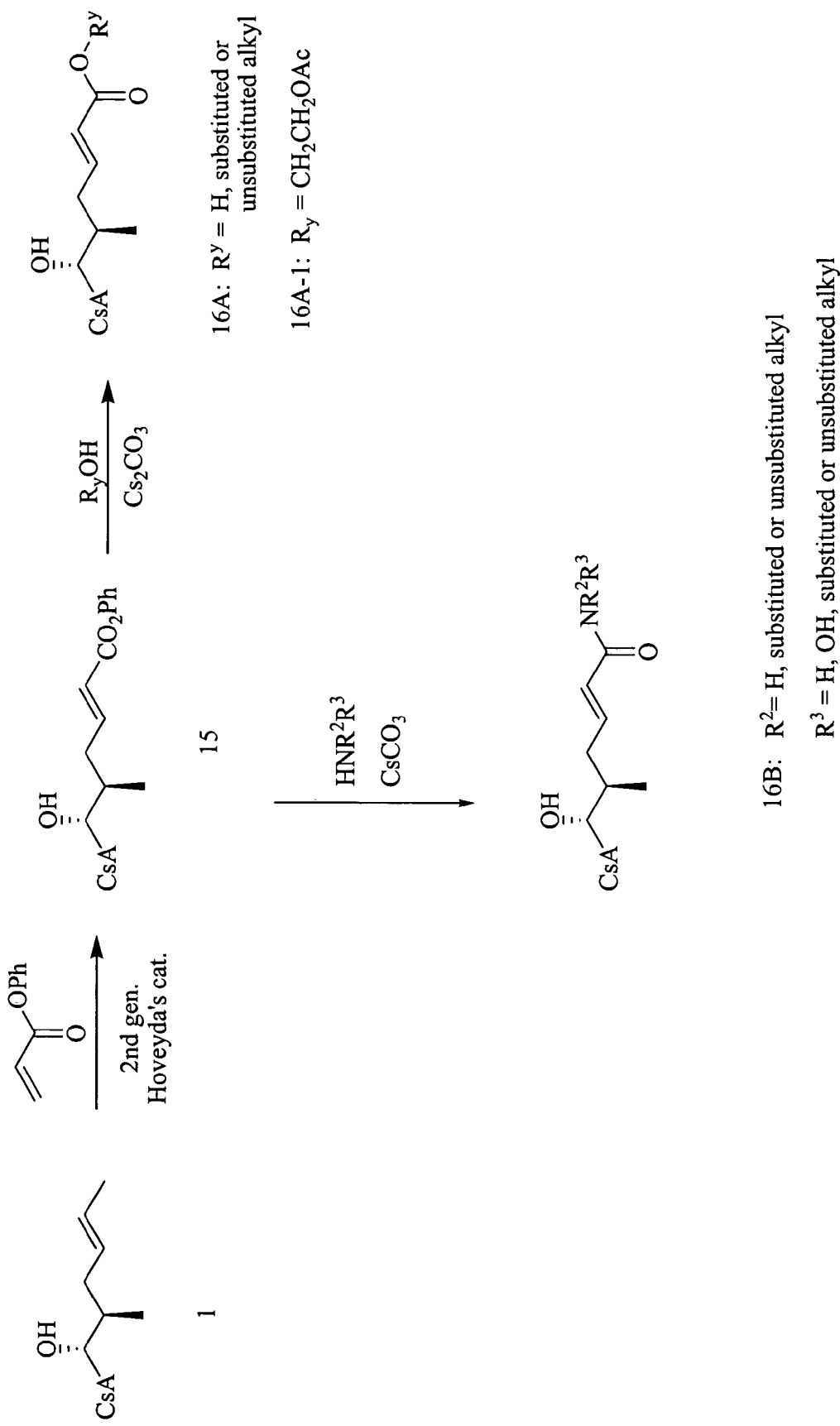
FIG. 2 shows a reaction scheme for the synthesis of compounds 16A, 16A-1, and 16B.

FIG. 2 shows the reaction scheme for the synthesis of compounds having the general formula 16A or 16B, obtained by the reaction of cyclosporin A or a cyclosporin derivative and phenyl acrylate catalyzed by Hoveyda's $2^{nd}$ generation catalyst to provide compound 15. Compound 15 is then converted to compound 16A or 16B by treating compound 15 with a compound having the formula $R^yOH$ or $HNR^xR^y$ and a base such as cesium carbonate, where $R^x$ is H, OH or a substituted or unsubstituted alkyl, and $R^y$ is H or a substituted or unsubstituted alkyl. The success of this reaction is based on the recognition by the inventors that compound 15 is a more reactive ester due to the phenyl group. This phenyl ester not only allows for a facile transesterification with improved yield and efficiency, but further allows for the easy conversion of the phenyl ester to an amide or hydroxamate without affecting the alkyl ester that is introduced as a result of the conversion (e.g., the acetate group of compound 16A).

Figure 3:
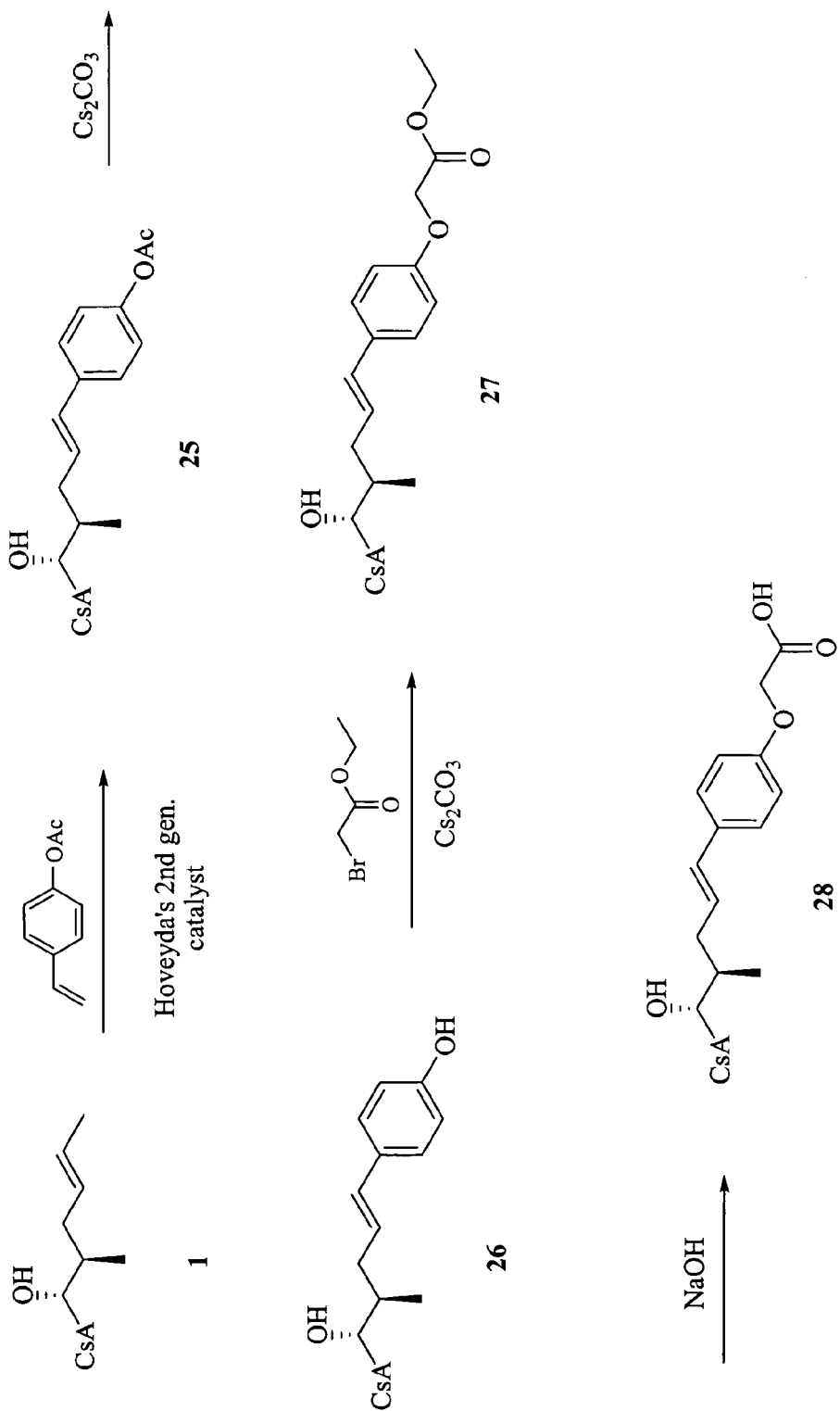
FIG. 3 shows a reaction scheme for the synthesis of compound 28.

FIG. 3 shows the reaction scheme for the synthesis of compound 28, the synthesis of which is described in Example 22.

Figure 4:
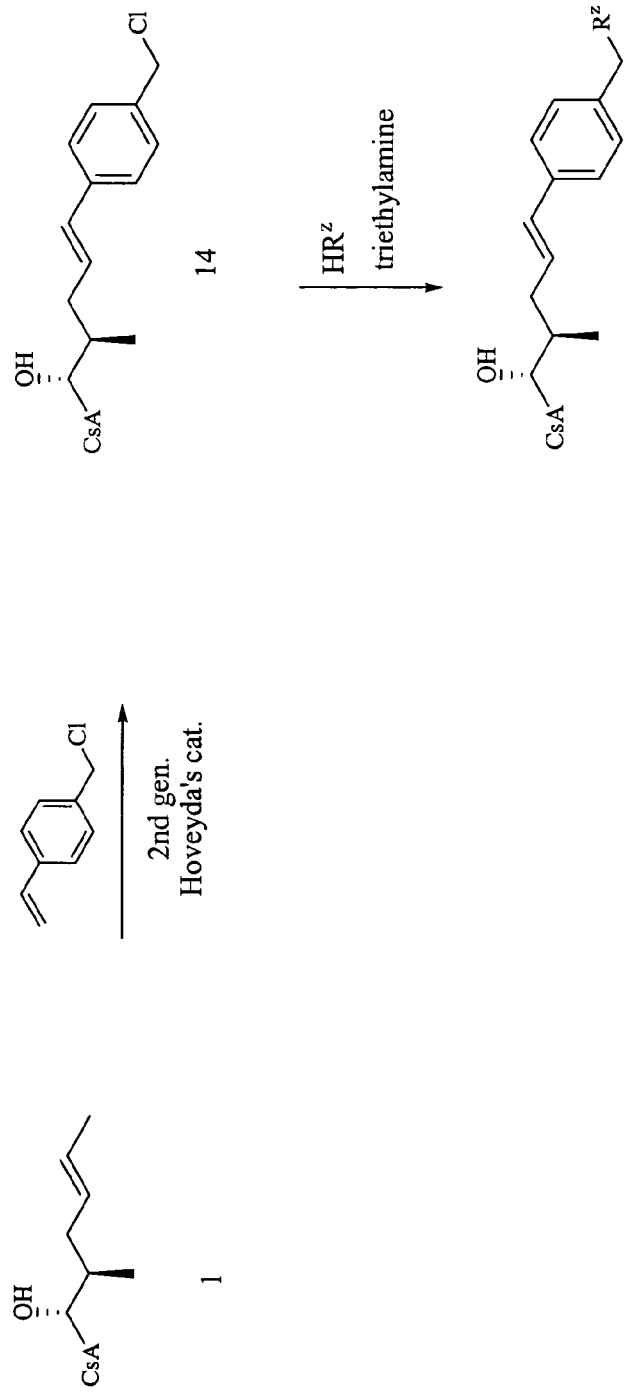
FIG. 4 shows a reaction scheme for the synthesis of compounds 38 and 38A.

FIG. 4 shows the reaction scheme for the synthesis of compound 38A, the synthesis of which is described in Example 32. The preparation of compound 38A utilizes the unique intermediate 14, which is a benzyl chloride that is suitably electrophilic and allows for the synthesis of a variety of compounds by reacting compound 14 with a nucleophile. Examples of suitable nucleophiles include, but are not limited to, aryl thiols, alkyl thiols, substituted alkyl thiols, amines, anilines, alcohols, phenols, and cyanide.

Figure 5:
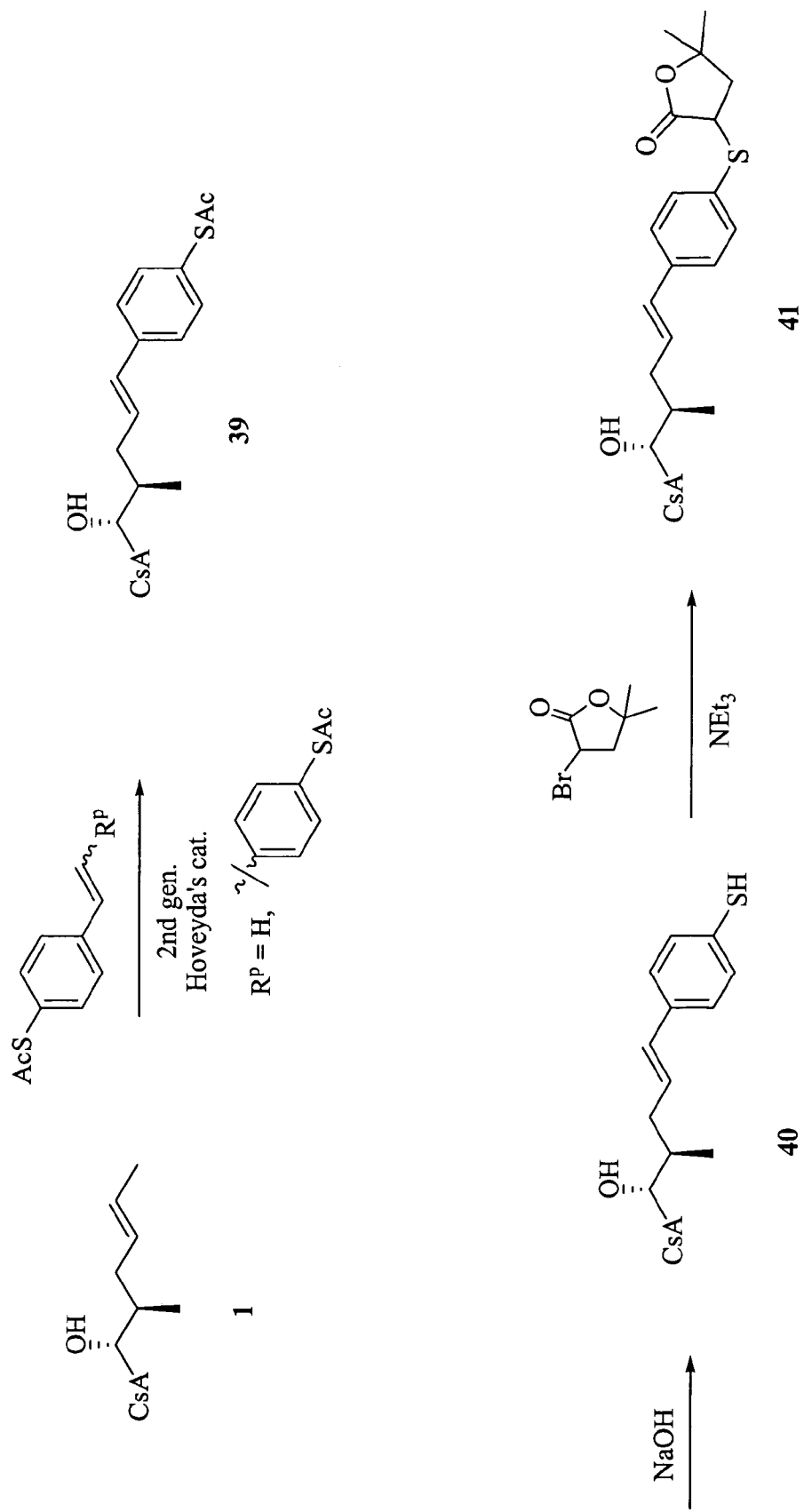
FIG. 5 shows a reaction scheme for the synthesis of compound 41.

FIG. 5 shows the reaction scheme for the synthesis of compound 41, the synthesis of which is described in Example 33. In general, the method comprises reacting cyclosporin A or a cyclosporin derivative with a substituted or unsubstituted styrene or stilbene in the presence of a suitable olefin metathesis catalyst such as, but limited to, a ruthenium metathesis catalyst such as benzylidenebis(tricyclohexylphosphine)-dichlororuthenium (Grubbs' first generation catalyst), 1,3-(bis(mesityl)-2-imidazolidinylidene) dichloro-(phenylmethylene)(tricyclohexylphosphine) ruthenium (Grubbs' second generation catalyst), or 1,3-(bis (mesityl)-2-imidazolidinylidene)dichloro-(o-isopropoxyphenylmethylene)ruthenium (Hoveyda-Grubbs' catalyst, also known as Hoveyda's second generation catalyst). For additional suitable catalysts, see M. Lautens and M. Maddess, *Organic Letters,* 2004, 6(12):1883–1886; J. Smulik and S. Diver, *Organic Letters,* 2002, 4(12):2051–2054; and R. Grubbs, *Tetrahedron,* 2004, 60:7117–7140.

Figure 6:
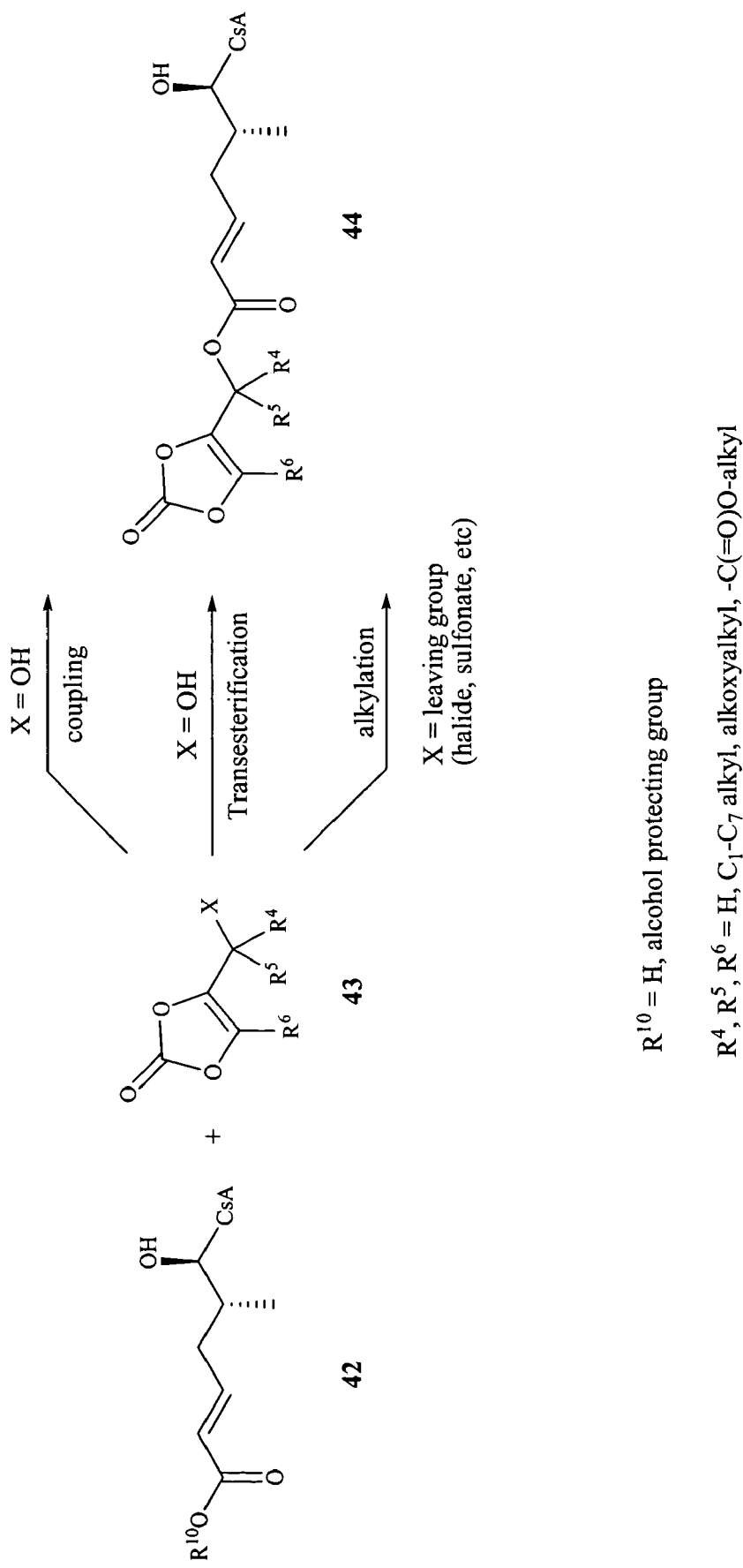
FIG. 6 shows several reaction schemes for the synthesis of compound 44.

FIG. 6 shows several reaction schemes for the synthesis of cyclic carbamate derivatives 44 of this invention. The cyclic carbamate can be prepared, for example, from the acid 43 and the alcohol 42 using standard coupling procedures, e.g., by alkylation of the acid 43 with an appropriate electrophile, or by transesterification.

Figure 7:
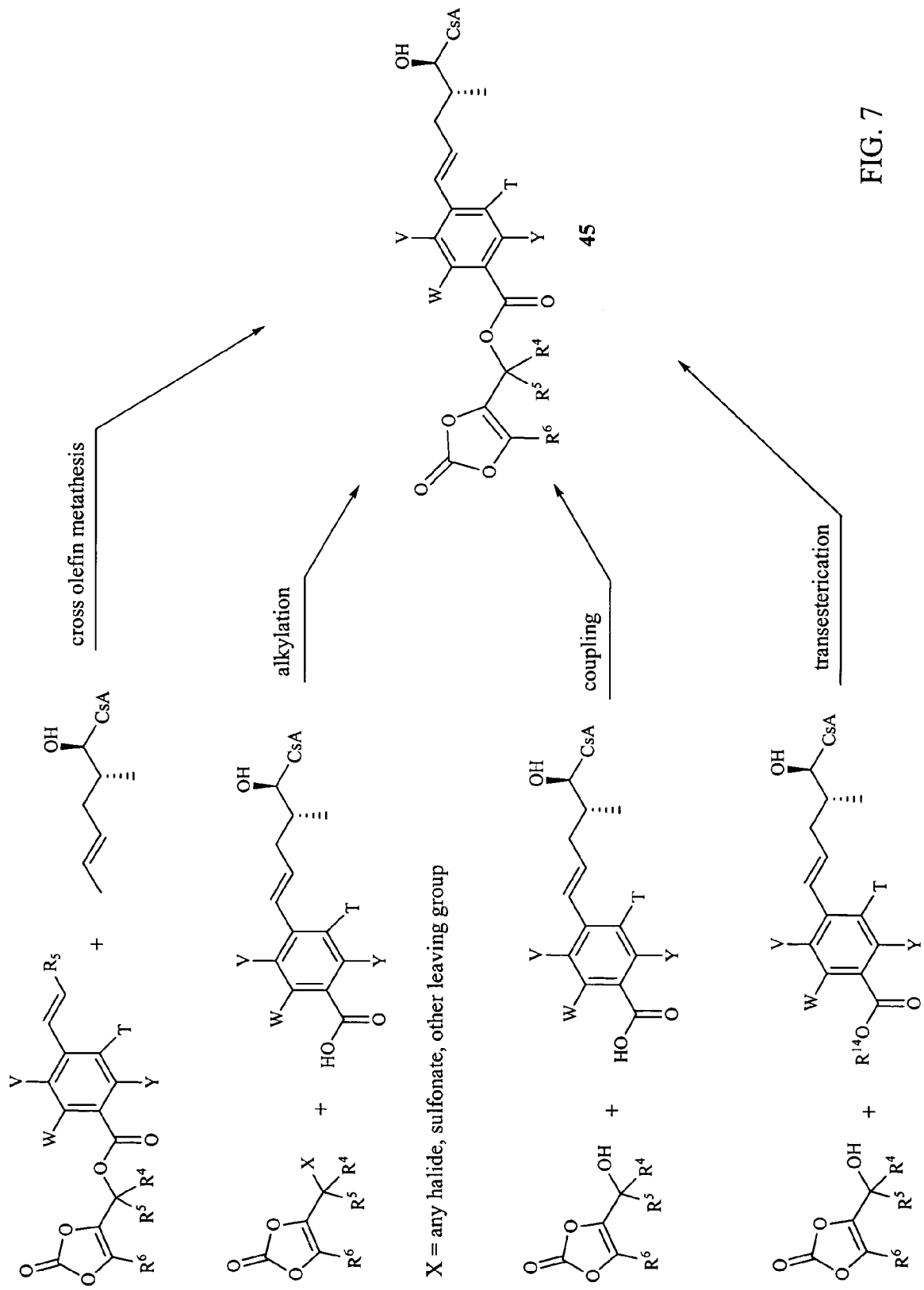
FIG. 7 shows several reaction schemes for the synthesis of compound 45.

FIG. 7 shows several reaction schemes for the synthesis of derivatives of this invention having the general formula 45. For example, the derivatives shown in FIG. 7 can be prepared from cyclosporin A or a cyclosporin derivative and an appropriate olefin by cross olefin metathesis, by alkylation of the acid with the appropriate electrophile, by coupling of the acid to the corresponding alcohol, or by transesterification.

Figure 8:
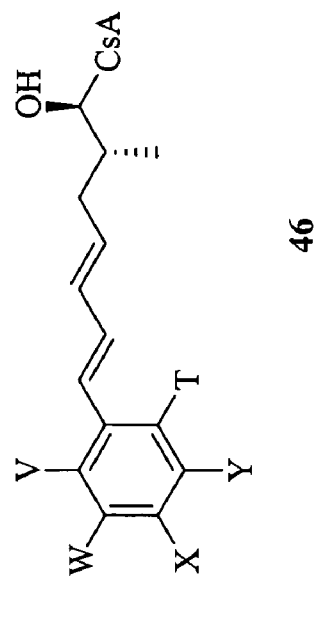
FIG. 8 shows a reaction scheme for the synthesis of compound 46.
Figure 8:
Figure 8:
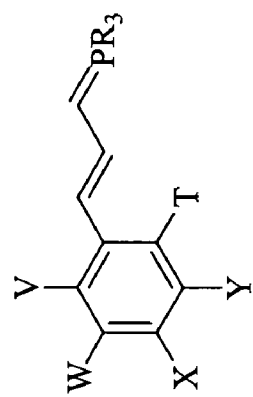
Figure 8:
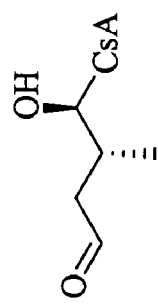

FIG. 8 shows the reaction scheme for the synthesis of derivatives of this invention having the general formula 46. This derivative can be prepared, for example, by a Wittig type reaction with the appropriate aldehyde.

The cyclosporins of the present invention are useful for the treatment of diseases or conditions responsive to or requiring anti-inflammatory, immunosuppressive, or related therapy, e.g. for topical administration for the treatment of such diseases or conditions of the eye, nasal passages, buccal cavity, colon, skin, intestinal tract, airway, lung, ear, anus or vagina. In particular, the cyclosporins of the present invention permit topical anti-inflammatory, immunosuppressive or related therapy with the concomitant reduction or minimization of undesirable systemic side effects such as general systemic immunosuppression.

Cyclosporins of the invention are useful, for example, for the treatment of diseases and conditions of the airways or lung, in particular inflammatory or obstructive airways disease. They are especially useful for the treatment of diseases or conditions of the airways or lung associated with or characterized by inflammatory cell infiltration or other inflammatory event accompanied by the accumulation of inflammatory cells, e.g., eosinophils and/or neutrophils.

The term "treating" as used herein, unless otherwise indicated, means reversing, alleviating, inhibiting the progress of, or preventing the disorder or condition to which such term applies, or one or more symptoms of such disorder or condition. The term "treatment," as used herein, unless otherwise indicated, refers to the act of treating as "treating" is defined immediately above. "Treating" is intended to mean at least the mitigation of a disease condition in a mammal, such as a human, particularly when the mammal is found to be predisposed to having the disease condition but has not yet been diagnosed as having it and includes, but is not limited to, modulating and/or inhibiting the disease condition; and/or alleviating the disease condition.

The cyclosporins of the invention are useful, for example, for the treatment of asthma of whatever type of genesis, including both intrinsic and, especially, extrinsic asthma. For example, they are useful for the treatment of atopic and non-atopic asthma, including allergic asthma, bronchitic asthma, exercise-induced asthma, occupational asthma, asthma induced following bacterial infection and other non-allergic asthmas. Treatment of asthma is also to be understood as embracing treatment of "wheezy-infant syndrome," that is treatment of subjects, e.g., of less than 4 to 5 years of age, exhibiting wheezing symptoms, in particular at night, and diagnosed or diagnosable as "wheezy infants," an established patient category of major medical concern and now more correctly identified as incipient or early-phase asthmatics. Cyclosporins of the invention are in particular useful for the treatment of asthma in subjects whose asthmatic status is either steroid-dependent or steroid-resistant.

Cyclosporins of the invention are also useful for the treatment of bronchitis or for the treatment of chronic or acute airways obstruction associated therewith. Cyclosporins of the invention may be used for the treatment of bronchitis of whatever type or genesis, including, for example, acute bronchitis, arachidic bronchitis, catarrhal bronchitis, chronic bronchitis, croupous bronchitis, phthinoid bronchitis and so forth.

Cyclosporins of the invention are in addition useful for the treatment of pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, berylliosis, chalicosis, ptilosis, siderosis, silicosis, tabacosis and, in particular, byssinosis.

Cyclosporins of the invention may also be used for the treatment of eosinophil-related disorders of the airways (e.g., involving morbid eosinophilic infiltration of pulmonary tissues) including hypereosinophilia as it affects the airways and/or lungs as well as, for example, eosinophil-related disorders of the airways consequential or concomitant to Loffler's Syndrome, eosinophilic pneumonia, parasitic (in particular metazoan) infestation (including tropical eosinophilia), bronchopulmonary aspergillosis, polyarteritis nodosa (including Churg-Strauss Syndrome), eosinophilic granuloma and eosinophil-related disorders affecting the airways occasioned by drug reaction.

Cyclosporins of the invention may also be used to treat any disease or condition of the airways or lung requiring immunosuppressive therapy, e.g., for the treatment of autoimmune diseases of, or as they affect, the lungs (for example, for the treatment of sarcoidosis, alveolitis or chronic hypersensitivity pneumonitis) or for the maintenance of allogenic lung transplant, e.g., following lung or heart lung transplantation.

When used in relation to the treatment of diseases of the airways and lungs, in particular asthma, the term "treatment" is to be understood as embracing both symptomatic and prophylactic modes, that is the immediate treatment, for example, of acute inflammation (symptomatic treatment) as well as advance treatment to prevent, ameliorate or restrict long term symptomatology (prophylactic treatment). For example, in the case of asthma, the present invention includes symptomatic treatment to ameliorate acute inflammatory events as well as prophylactic treatment to inhibit on-going inflammatory status and to ameliorate future bronchial exacerbation associated therewith.

The present invention further relates to a method of preventing or treating an inflammatory or autoimmune disorder in a subject, while eliminating or reducing the toxicity associated with the administration of cyclosporin A, through the systemic administration of a therapeutically effective amount of a pharmaceutical composition comprising at least one compound of Formula I or a metabolite, solvate, resolved enantiomer, diastereomer, racemic mixture or pharmaceutically acceptable salt thereof. Inflammatory or immune disorders that can be treated by the cyclosporins of the present invention include, but are not limited to, rheumatoid arthritis, inflammatory bowel disease, psoriasis, atopic dermatitis, asthma, allergic rhinitis, and chronic obstructive pulmonary disease.

The present invention also provides methods of prevention of organ transplantation rejection in a subject by administering to the subject therapeutically effective amounts of one or more of the cyclosporin analogs of the present invention with or without the concurrent use of other known treatments.

As immunosuppressants, the compounds of Formula I are useful when administered for the prevention of immune-mediated tissue or organ graft rejection. Examples of transplanted tissues and organs which suffer from these effects are heart, kidney, liver, medulla ossium, skin, cornea, lung, pancreas, intestinum tenue, limb, muscle, nervus, duodenum, small-bowel, pancreatic-islet-cell, and the like; as well as graft-versus-host diseases brought about by medulla ossium transplantation. The regulation of the immune response by the compounds of the invention would also find utility in the treatment of autoimmune diseases, such as rheumatoid arthritis, systemic lupus erythematosis, hyper-immunoglobulin E, Hashimoto's thyroiditis, multiple sclerosis, progressive systemic sclerosis, myasthenia gravis, type I diabetes, uveitis, allergic encephalomyelitis, glomerulonephritis, and the like; and further infectious diseases caused by pathogenic microorganisms, such as HIV. In the particular cases of HIV-1, HIV-2 and related retroviral strains, inhibition of T-cell mitosis would suppress the replication of the virus, since the virus relies upon the host T-cell's proliferative functions to replicate.

Cyclosporins of the invention may be administered by routes including, but not limited to, the pulmonary route (inhalation), nasal administration, rectal administration (e.g. suppository or enema form), dermally (topically to the skin), orally or ophthalmically. When administrated, the cyclosporins of the invention will have potent efficacy at the site(s) of administration, while devoid of, or exhibit relatively reduced, systemic activity.

For example, certain compounds of Formula I can be administered topically within the airways, e.g. by the pulmonary route, by inhalation. While having potent efficacy when administered topically, cyclosporins of the invention are devoid of, or exhibit relatively reduced, systemic activity, e.g. following oral administration. Cyclosporins of the invention thus provide a means for the treatment of diseases and conditions of the airways or lung with the avoidance of unwanted systemic side effect, e.g., consequent to inadvertent swallowing of drug substance during inhalation therapy.

Compounds of Formula I can also be administered dermally, i.e. topically to the skin, for example for the treatment of cutaneous diseases mediated by immune mechanisms, e.g., psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lumpus erythematosus, pemphisus, epidermolysis bullosa acquisita, and other inflammatory or allergic conditions of the skin. Optionally, the cyclosporins of the invention are co-administered together with anti-inflammatory, immunosuppressive, or other pharmacologically active agents, e.g., corticosteroids, antihistamines, antibiotics, antifungals, etc.

In order to use a compound of the Formula I, it is normally formulated in accordance with standard pharmaceutical practice as a pharmaceutical composition. According to this aspect of the invention there is provided a pharmaceutical composition that comprises a compound of the Formula I, or a pharmaceutically acceptable salt thereof, in association with a pharmaceutically acceptable diluent or carrier.

To prepare the pharmaceutical compositions according to this invention, a therapeutically or prophylactically effective amount of a compound of Formula I or pharmaceutically acceptable salt, solvate, or metabolite thereof (alone or together with an additional therapeutic agent as disclosed herein) is intimately admixed, for example, with a pharmaceutically acceptable carrier according to conventional pharmaceutical compounding techniques to produce a dose. A carrier may take a wide variety of forms depending on the form of preparation desired for administration, e.g., oral or parenteral. Examples of suitable carriers include, but are not limited to, any and all solvents, dispersion media, adjuvants, coatings, antibacterial and antifungal agents, isotonic and absorption delaying agents, sweeteners, stabilizers (to promote long term storage), emulsifiers, binding agents, thickening agents, salts, preservatives, solvents, dispersion media, coatings, antibacterial and antifungal agents, isotonic and absorption delaying agents, flavoring agents, and miscellaneous materials such as buffers and absorbents that may be needed in order to prepare a particular therapeutic composition. The use of such media and agents with pharmaceutically active substances is well known in the art. Except insofar as any conventional media or agent is incompatible with a compound of Formula I, its use in the therapeutic compositions and preparations is contemplated. Supplementary active ingredients can also be incorporated into the compositions and preparations as described herein.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, or intramuscular dosing or as a suppository for rectal dosing). For example, compositions intended for oral use may contain, for example, one or more coloring, sweetening, flavoring and/or preservative agents.

Suitable pharmaceutically-acceptable excipients for a tablet formulation include, for example, inert diluents such as lactose, sodium carbonate, calcium phosphate or calcium carbonate, granulating and disintegrating agents such as corn starch or algenic acid; binding agents such as starch;

lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), coloring agents, flavoring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavoring and coloring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient that is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedures well known in the art.

Compositions for administration by insufflation may be in the form of a finely divided powder containing particles of average diameter of, for example, 30 µm or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurized aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

Use of controlled-release oral dosage forms that comprise a tablet or capsule containing a plurality of particles of a cyclosporin of this invention dispersed in a swellable/erodible polymer may be used. Further, controlled release oral dosage forms of the cyclosporins of the invention may be used for continuous, sustained administration to the upper gastrointestinal tract of a patient. The majority of the dose of cyclosporins of the invention may be delivered, on an extended release basis, to the stomach, duodenum, and upper regions of the small intestine, with delivery of the drug to the lower gastrointestinal tract and colon substantially restricted. A variety of technologies, including hydrophilic, water-swellable, crosslinked, polymers that maintain physical integrity over the dosage lifetime but thereafter rapidly dissolve may be utilized for delivery of the cyclosporins of the invention.

For further information on formulations, see Chapter 25.2 in Volume 5 of Comprehensive Medicinal Chemistry (Corwin Hansch; Chairman of Editorial Board), Pergamon Press 1990, which is specifically incorporated herein by reference.

It will be understood that the specific dosage level and frequency of dosage therapeutic or prophylactic purposes for any particular subject may be varied and will depend upon a variety of factors including the activity of the specific compound of Formula I, the species, age, body weight, general health, sex and diet of the subject, the rate, mode and time of administration, rate of excretion, drug combination, severity of the particular condition, and the discretion of the prescribing physician, but can nevertheless be routinely determined by one skilled in the art. In one embodiment, an effective dosage is in the range of about 0.001 to about 100 mg per kg body weight per day, for example, about 0.5 to about 35 mg/kg/day, in single or divided doses. For a 70 kg human, this would amount to about 0.0035 to 2.5 g/day, such as about 0.05 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day. For further information on routes of administration and dosage regimes, see Chapter 25.3 in Volume 5 of Comprehensive Medicinal Chemistry (Corwin Hansch; Chairman of Editorial Board), Pergamon Press 1990, which is specifically incorporated herein by reference.

This invention further provides a compound of Formula I or a metabolite, solvate, resolved enantiomer, diastereomer, racemic mixture or pharmaceutically acceptable salt thereof for use as a medicament in the treatment of the diseases or conditions described above in a warm-blooded animal, such as a mammal, for example, a human, suffering from such disease or condition. Also provided is the use of a compound of Formula I or a metabolite, solvate, resolved enantiomer, diastereomer, racemic mixture or pharmaceutically acceptable salt thereof in the preparation of a medicament for the treatment of the diseases and conditions described above in a warm-blooded animal, such as a mammal, for example a human, suffering from such disorder.

In another embodiment of the invention, an article of manufacture, or "kit", containing materials useful for the treatment of the disorders described above is provided. In one embodiment, the kit comprises a container comprising a compound of Formula I. In one embodiment, the invention provides a kit for treating immunoregulatory or respiratory diseases, disorders, or conditions. Suitable containers include, for example, bottles, vials, syringes, blister pack, etc. The container may be formed from a variety of materials such as glass or plastic. The container holds a compound of Formula I or a pharmaceutical formulation thereof, in an amount effective for treating the condition, and may have a sterile access port (for example, the container may be an intravenous solution bag or a vial having a stopper pierceable by a hypodermic injection needle). The kit may further comprise a label or package insert on or associated with the container. The label or package insert indicates that the composition is used for treating the condition of choice. Alternatively, or additionally, the kit may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of Formula I and, if present, the second pharmaceutical formulation for treating or preventing an immunoregulatory or respiratory disease, disorder or condition. For example, if the kit comprises a first composition comprising a compound of Formula I and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a compound of Formula I, such as tablets or capsules. Such a kit includes, for example, a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, the kit may comprise (a) a first container with a compound of Formula I contained therein; and optionally (b) a second pharmaceutical formulation, wherein the second pharmaceutical formulation comprises a second compound for treatment of the immunoregulatory or respiratory disease, disorder, or condition. Alternatively, or additionally, the kit may further comprise a third container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a pharmaceutical formulation of a compound of Formula I and a second formulation comprising a second therapeutic agent, the kit may comprise a separate container for containing the separate formulations, such as a divided bottle or a divided foil packet; however, the separate compositions may also be contained within a single, undivided container. Typically, the kit comprises directions for the administration of the separate components. The kit form is particularly advantageous when the separate components are administered in different dosage forms (e.g., oral and parenteral), are administered at different dosage intervals, or when titration of the individual components of the combination is desired by the prescribing physician.

In order to illustrate the invention, the following examples are included. However, it is to be understood that these examples do not limit the invention and are only meant to suggest a method of practicing the invention. Persons skilled in the art will recognize that the chemical reactions described may be readily adapted to prepare a number of other cyclosporin analogs of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

EXAMPLES

In the examples described below, unless otherwise indicated all temperatures are set forth in degrees Celsius.

Reagents were purchased from commercial suppliers such as Aldrich Chemical Company, Lancaster, TCI or Maybridge, and were used without further purification unless otherwise indicated. Tetrahydrofuran (THF), N,N-dimethylformamide (DMF), dichloromethane (DCM), toluene, dioxane and 1,2-difluoroethane were purchased from Aldrich in Sure seal bottles and used as received. Hoveyda's $2^{nd}$ generation catalyst was purchased from Aldrich.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Example 1

Procedure A: Synthesis of Compound 3

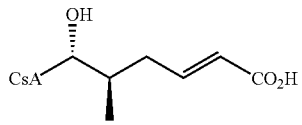

The reaction scheme for the synthesis of compound 3 according to procedure A is shown in FIG. 1.

Step 1: Synthesis of compound 2: To a solution of cyclosporin A (1.61 g, 1.34 mmol) in dichloromethane (3.4 mL) under $N_2$ atmosphere was added t-butyl acrylate (2.57 g, 20.1 mmol) and Hoveyda's $2^{nd}$ generation catalyst (84 mg, 0.13 mmol). The resulting green solution was heated to reflux under nitrogen for 16 hours. The reaction mixture was chromatographed on silica eluting with a gradient of dichloromethane, dichloromethane/MeOH (40:1), dichloromethane/MeOH (20:1), to afford 1.60 g of compound 2 as a gray solid (93% yield). MS (APCI+) m/z 1288 (M+1) detected.

Step 2: Synthesis of compound 3: A solution of compound 2 (0.054 g, 0.042 mmol) in dichloromethane/TFA (4 mL, 1:1) was stirred at room temperature for 2 hours. The mixture was concentrated under reduced pressure and chromatographed on silica eluting with 10% acetonitrile in ethyl acetate with 0.25% acetic acid. The desired compound 3 was obtained in 48% yield. MS (APCI−) m/z 1231 (M−1) detected.

Example 2

Synthesis of Compound 4

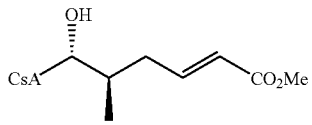

Prepared according to Procedure A, Step 1 from cyclosporin A and methyl maleate. The crude product was chromatographed on silica eluting with a gradient of dichloromethane, 2.5% MeOH in dichloromethane, 5% MeOH in dichloromethane to afford compound 4 as a pale gray solid (88% yield). MS (APCI+) m/z 1246 (M+1) detected.

Example 3

Synthesis of Compound 5

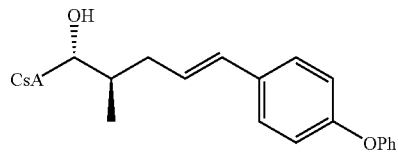

Prepared according to Procedure A, Step 1 from cyclosporin A and 4-phenoxystyrene. The crude product was chromatographed on silica eluting with a gradient of dichloromethane, dichloromethane/MeOH (40:1) and dichloromethane/MeOH (20:1) to afford compound 5 in 98% yield. MS (APCI+) m/z 1357 (M+1) detected.

Example 4

Synthesis of Compound 6

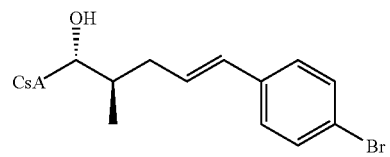

Prepared according to Procedure A, Step 1 from cyclosporin A and 4-bromostyrene. The crude product was chromatographed on silica eluting with a gradient of dichloromethane, dichloromethane/MeOH (97.5:2.5) and dichloromethane/MeOH (95:5) to afford compound 6 in 94% yield. MS (APCI+) m/z 1342, 1344 (M+1; Br pattern) detected.

Example 5

Synthesis of Compound 7

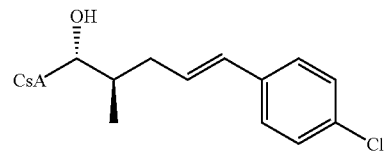

Prepared according to Procedure A, Step 1 from cyclosporin A and 4-chlorostyrene. The crude product was chromatographed on silica eluting with a gradient of dichloromethane, dichloromethane/MeOH (40:1) and dichloromethane/MeOH (20:1) to afford compound 7 in 94% yield. MS (APCI+) m/z 1298, 1300 (M+1; Cl pattern) detected.

Example 6

Synthesis of Compound 8

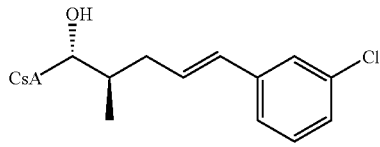

Prepared according to Procedure A, Step 1 from cyclosporin A and 3-chlorostyrene. The crude product was chromatographed on silica eluting with a gradient of dichloromethane, dichloromethane/MeOH (40:1) and dichloromethane/MeOH (20:1) to afford compound 8 in 97% yield. MS (APCI+) m/z 1298, 1300 (M+1; Cl pattern) detected.

Example 7

Synthesis of Compound 9

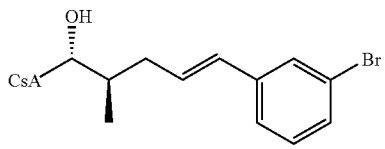

Prepared according to Procedure A, Step 1 from cyclosporin A and 3-bromostyrene. The crude product was chromatographed on silica eluting with a gradient of dichloromethane, dichloromethane/MeOH (98:2), dichloromethane/MeOH (96.5:3.5) and dichloromethane/MeOH (95:5) to afford compound 9 in 91% yield. MS (ESI+) m/z 1342, 1344 (M+1; Br pattern) detected.

Example 8

Synthesis of Compound 10

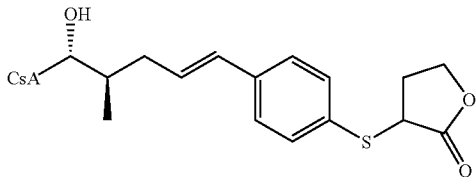

Prepared according to Procedure A, Step 1 from cyclosporin A and 3-(4-vinylphenylsulfanyl)-dihydrofuran-2-one. The crude product was chromatographed on silica eluting with a gradient of dichloromethane, dichloromethane/MeOH (97.5:2.5) and dichloromethane/MeOH (95:5). The residue was then purified by reverse phase HPLC to afford compound 10 in 67% yield. MS (APCI+) m/z 1380 (M+1) detected.

Example 9

Synthesis of Compound 11

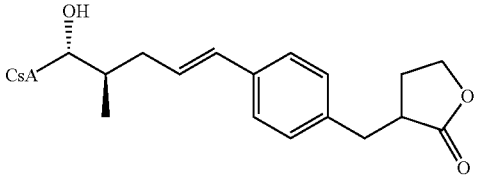

Prepared according to Procedure A, Step 1 from cyclosporin A and 3-(4-vinylbenzyl)-dihydrofuran-2-one. The crude product was chromatographed on silica eluting with a gradient of 2–6% MeOH in dichloromethane. The residue was then purified by reverse phase HPLC to afford compound 11 in 41% yield. MS (APCI−) m/z 1361 (M−1) detected.

Example 10

Synthesis of Compound 12

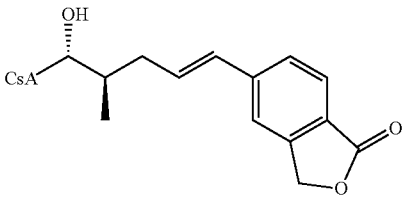

Prepared according to Procedure A, Step 1 from cyclosporin A and 5-vinyl-3H-isobenzofuran-1-one. The crude product was chromatographed on silica eluting with a gradient of dichloromethane, dichloromethane/MeOH (97.5:2.5) and dichloromethane/MeOH (95:5). The residue was then purified by reverse phase HPLC to afford compound 12 in 36% yield. MS (APCI+) m/z 1320 (M+1) detected.

Example 11

Synthesis of Compound 13

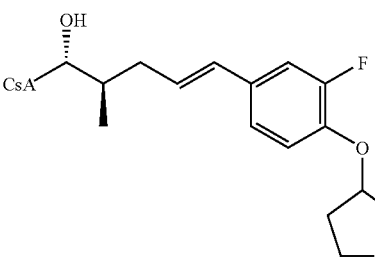

Prepared according to Procedure A, Step 1 from cyclosporin A and 3-(2-fluoro-4-vinylphenoxy)-dihydrofuran-2-one. The crude product was chromatographed on silica with a gradient of 2–6% MeOH in dichloromethane. The residue was then purified by reverse phase HPLC to afford compound 13 in 73% yield. MS (APCI−) m/z 1380 (M−1) detected.

Example 12

Synthesis of Compound 14

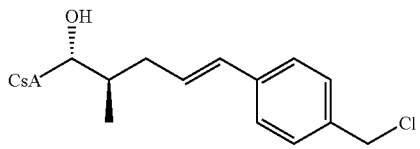

Prepared according to Procedure A, Step 1 from cyclosporin A and 4-chlorostyrene. The crude product was chromatographed on silica eluting with a gradient of 2–4% MeOH in dichloromethane. The residue was then purified by reverse phase HPLC to afford compound 14 in 34% yield. MS (APCI−) m/z 1314.6 (M+1) detected.

Example 13

Procedure B: Synthesis of Compound 16A-1

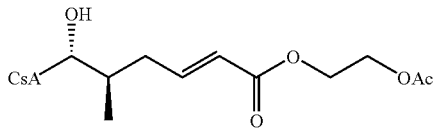

The reaction scheme for the synthesis of compound 16A-1 according to procedure B is shown in FIG. 2.

Step 1: Synthesis of compound 15: Prepared according to Procedure A, Step 1 from cyclosporin A and phenyl acrylate. The crude product was chromatographed on silica eluting with a gradient of dichloromethane, dichloromethane/MeOH (40:1), dichloromethane/MeOH (20:1), to afford compound 15 as a gray solid (95% yield). MS (APCI+) m/z 1308 (M+1) detected.

Step 2: Synthesis of compound 16A-1: A solution of compound 15 (0.043 g, 0.033 mmol) and ethylene glycol monoacetate (technical grade containing 25% ethylene glycol and 25% ethylene glycol diacetate, 0.068 g, 0.66 mmol) in dioxane (0.30 mL) was treated with $Cs_2CO_3$ (0.015 g, 0.046 mmol). The reaction vial was capped and heated to 50° C. for 1 hour. The cooled solution was chromatographed on silica packed with ethyl acetate/hexanes (1:1), eluting with a gradient of ethyl acetate/hexanes (1:1), ethyl acetate/hexanes (7:3), ethyl acetate, 3% MeOH in ethyl acetate. Compound 16A-1 was obtained as white solid (22 mg, 51% yield). MS (APCI+) m/z 1318 (M+1) detected.

Example 14

Synthesis of Compound 17

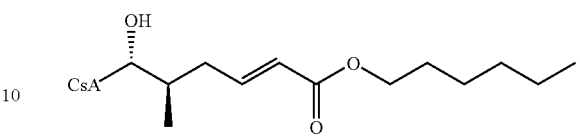

Prepared according to Procedure B, Step 2 from compound 15 (Example 13) and hexan-1-ol. The crude product was chromatographed on silica packed with ethyl acetate/hexanes (1:1), eluting with a gradient of ethyl acetate/hexanes (1:1), ethyl acetate, and 4% MeOH in ethyl acetate to provide compound 17 in 90% yield. MS (APCI+) m/z 1316 (M+1) detected.

Example 15

Synthesis of Compound 18

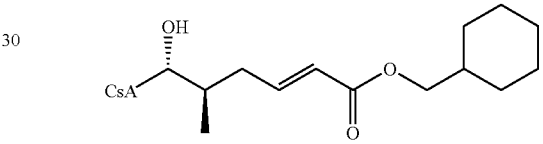

Prepared according to Procedure B, Step 2 from compound 15 (Example 13) and cyclohexyhmethanol. The crude mixture was partitioned between 1N NaOH and chloroform and the organic layer was dried, filtered and concentrated under reduced pressure. The residue was chromatographed on silica packed with ethyl acetate/hexanes (1:1), eluting with a gradient of ethyl acetate/hexanes (1:1), ethyl acetate, and 4% MeOH in ethyl acetate to provide compound 18 in 91% yield. MS (APCI+) m/z 1328 (M+1) detected.

Example 16

Synthesis of Compound 19

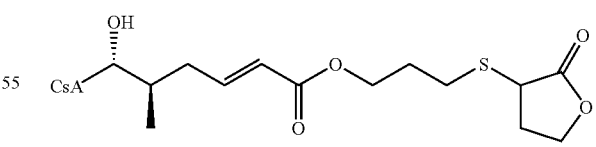

Prepared according to Procedure B, Step 2 from compound 15 (Example 13) and 3-(3-hydroxypropylsulfanyl)-dihydrofuran-2-one. The reaction mixture was heated to 70° C. for 30 hours. The crude product was chromatographed on silica packed with ethyl acetate/hexanes (1:1), eluting with a gradient of ethyl acetate/hexanes (1:1), ethyl acetate, and 4% MeOH in ethyl acetate to provide compound 19 in 49% yield. MS (APCI+) m/z 1390 (M+1) detected.

Example 17

Synthesis of Compound 20

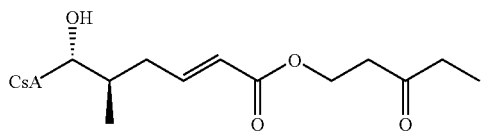

Prepared according to Procedure B, Step 2 from compound 15 (Example 13) and 6-hydroxyhexan-3-one. The crude product was chromatographed on silica packed with ethyl acetate/hexanes (1:1), eluting with a gradient of ethyl acetate/hexanes (1:1), ethyl acetate, and 4% MeOH in ethyl acetate to provide compound 20 in 72% yield. MS (APCI+) m/z 1316 (M+1) detected.

Example 18

Synthesis of Compound 21

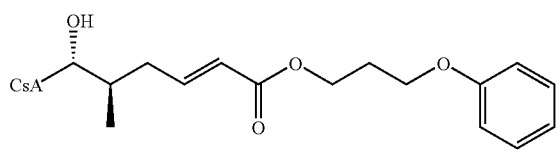

Prepared according to Procedure B, Step 2 from compound 15 (Example 13) and 3-phenoxypropan-1-ol. The crude product was chromatographed on silica packed with ethyl acetate/hexanes (1:1); eluting with a gradient of ethyl acetate/hexanes (1:1), ethyl acetate, and 4% MeOH in ethyl acetate to provide compound 21 in 90% yield. MS (APCI+) m/z 1366 (M+1) detected.

Example 19

Synthesis of Compound 22

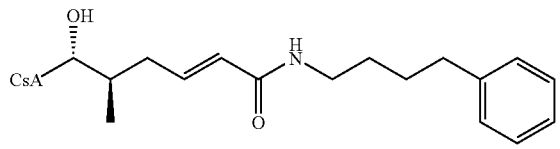

Prepared according to Procedure B, Step 2 from compound 15 (Example 13) and 4-phenylbutylamine. The crude product was chromatographed on silica packed with ethyl acetate/hexanes (1:1), eluting with a gradient of ethyl acetate/hexanes (1:1), ethyl acetate, 4% MeOH in ethyl acetate. Compound 22 was obtained as white solid (50% yield). MS (APCI+) m/z 1363 (M+1) detected.

Example 20

Synthesis of Compound 23

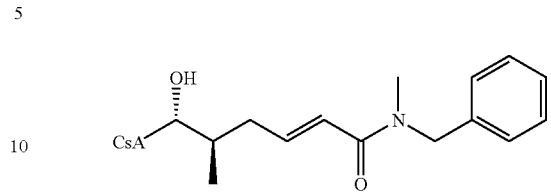

Prepared according to Procedure B, Step 2 from compound 15 (Example 13) and benzylmethylamine. The crude product was chromatographed on silica packed with ethyl acetate/hexanes (1:1), eluting with a gradient of ethyl acetate/hexanes (1:1), ethyl acetate, and 4% MeOH in ethyl acetate. Compound 23 was obtained in 99% yield. MS (APCI−) m/z 1334 (M−1) detected.

Example 21

Synthesis of Compound 24

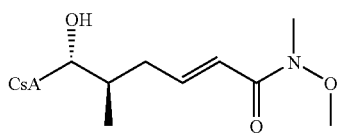

Prepared according to Procedure B, Step 2 from compound 15 (Example 13) and O,N-dimethylhydroxylamine hydrochloride. DMA was added to the mixture for solubility and the reaction was heated to 70° C. for 48 hours. The crude product was chromatographed on silica packed with ethyl acetate/hexanes (1:1), eluting with a gradient of ethyl acetate/hexanes (1:1), ethyl acetate, and 4% MeOH in ethyl acetate. Compound 24 was obtained in 35% yield. MS (APCI+) m/z 1275 (M+1) detected.

Example 22

Procedure C: Synthesis of Compound 28

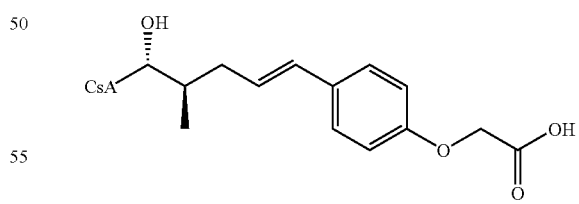

The reaction scheme for the synthesis of compound 28 according to procedure C is shown in FIG. 3.

Step 1: Synthesis of compound 25: Prepared according to Procedure A, Step 1 from cyclosporin A and 4-acetoxystyrene. The crude product was chromatographed on silica eluting with a gradient of dichloromethane, dichloromethane/MeOH (40:1), dichloromethane/MeOH (20:1), to afford compound 25 (99% yield). MS (APCI+) m/z 1322 (M+1) detected.

Step 2: Synthesis of compound 26: A solution of compound 25 (4.82 g, 3.64 mmol) in THF: ethanol (1:1) was treated with Cs$_2$CO$_3$ (1.60 g, 4.92 mmol) at room temperature for 5 hours. The reaction mixture was filtered through Celite and concentrated under reduced pressure. The residue was chromatographed on silica eluting with a gradient of dichloromethane, 2.5% MeOH in dichloromethane, and 5% MeOH in dichloromethane to provide 4.43 g of compound 26 (95% yield). MS (ESI+) m/z 1280 (M+1) detected.

Step 3: Synthesis of compound 27: To a solution of compound 26 (0.047 g, 0.037 mmol) in ethanol (0.37 mL) was added ethyl bromoacetate (0.016 g, 0.096 mmol). The mixture was stirred at room temperature for 16 hours. The reaction mixture was chromatographed on silica eluting with a gradient of 25% ethyl acetate in hexanes, 65% ethyl acetate in hexanes, and 5% MeOH in ethyl acetate to afford 41 mg of compound 27 as a white solid (81% yield). MS (APCI+) m/z 1366 (M+1) detected.

Step 4: Synthesis of compound 28: A solution of compound 27 (0.025 g, 0.018 mmol) in THF/MeOH (3:1) was treated with 5N NaOH (5 equiv.) at room temperature for 2 hours. The mixture was quenched with 5N HCl, concentrated under reduced pressure and purified by reverse phase HPLC to afford 9.3 mg of compound 28 as a white solid (38% yield). MS (ESI+) m/z 1338 (M+1) detected.

Example 23

Synthesis of Compound 29

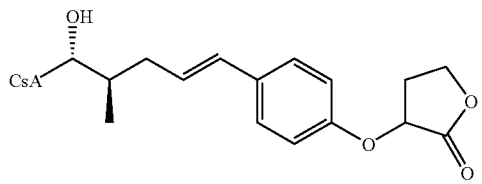

Prepared according to Procedure C, Step 3, from compound 26 (Example 22) and 3-bromodihydrofuran-2-one. The crude product was purified by reverse phase HPLC to afford 17 mg of compound 29 as a white solid (32% yield). MS (ESI+) m/z 1364 (M+1) detected.

Example 24

Synthesis of Compound 30

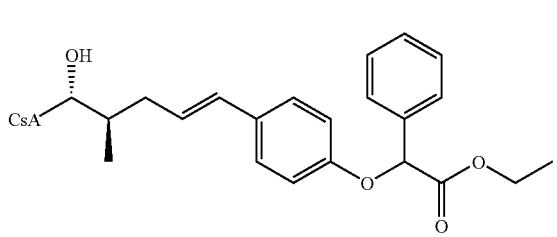

Prepared according to Procedure C, Step 3, from compound 26 (Example 22) and bromophenylacetic acid ethyl ester. The crude product was purified by reverse phase HPLC to afford compound 30 (23% yield). MS (APCI+) m/z 1442 (M+1) detected.

Example 25

Synthesis of Compound 31

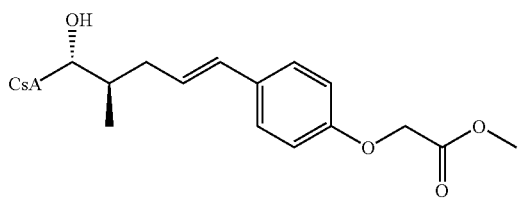

Prepared according to Procedure C, Step 3 from compound 26 (Example 22) and bromoacetic acid methyl ester. The crude product was purified by reverse phase HPLC to afford compound 31 (45% yield). MS (APCI+) m/z 1352 (M+1) detected.

Example 26

Synthesis of Compound 32

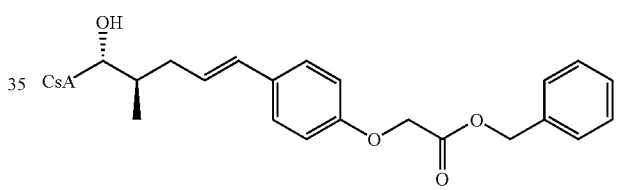

Prepared according to Procedure C, Step 3, from compound 26 (Example 22) and bromoacetic acid benzyl ester. The crude product was purified by reverse phase HPLC to afford compound 32 (15% yield). MS (APCI+) m/z 1428 (M+1) detected.

Example 27

Synthesis of Compound 33

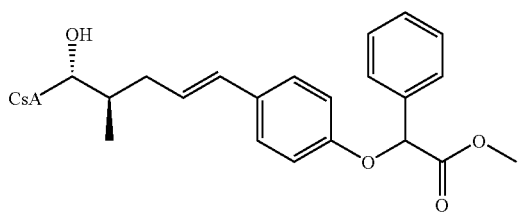

Prepared according to Procedure C, Step 3, from compound 26 (Example 22) and bromophenylacetic acid methyl ester. The crude product was purified by reverse phase HPLC to afford compound 33 (25% yield). MS (ESI+) m/z 1428 (M+1) detected.

Example 28

Synthesis of Compound 34

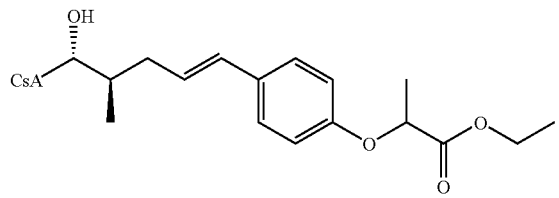

Prepared according to Procedure C, Step 3, from compound 26 (Example 22) and 2-bromopropionic acid ethyl ester. The crude product was purified by reverse phase HPLC to afford compound 34 (32% yield). MS (ESI+) m/z 1380 (M+1) detected.

Example 29

Synthesis of Compound 35

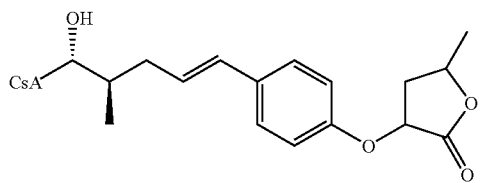

Prepared according to Procedure C, Step 3, from compound 26 (Example 22) and 3-bromo-5-methyldihydrofuran-2-one. The crude product was purified by reverse phase HPLC to afford compound 35 (46% yield). MS (APCI+) m/z 1378 (M+1) detected.

Example 30

Synthesis of Compound 36

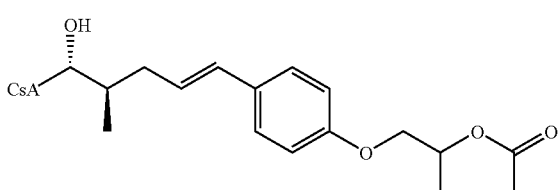

Prepared according to Procedure C, Step 3, from compound 26 (Example 22) and 6-iodomethyltetrahydropyran-2-one. The crude product was purified by reverse phase HPLC to afford compound 36 (29% yield). MS (APCI−) m/z 1391 (M−1) detected.

Example 31

Synthesis of Compound 37

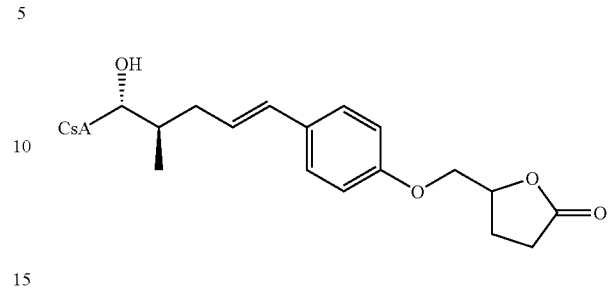

Prepared according to Procedure C, Step 3, from compound 26 (Example 22) and 5-iodomethyldihydrofuran-2-one. The crude product was purified by reverse phase HPLC to afford compound 37 (30% yield). MS (APCI−) m/z 1377 (M−1) detected.

Example 32

Procedure D: Synthesis of Compound 38A

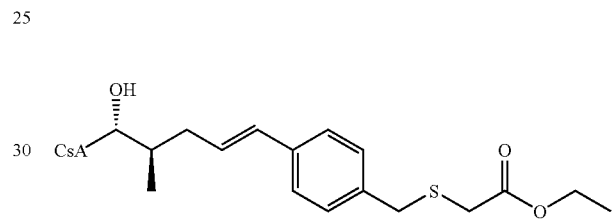

The reaction scheme for the synthesis of compound 38A according to procedure D is shown in FIG. 4.

Step 1: Synthesis of compound 14: Compound 14 was prepared as described in Example 12.

Step 2: Synthesis of compound 38A: To a solution of compound 14 (50 mg, 0.038 mmol) in acetone (0.381 mL) under $N_2$ atmosphere was added triethylamine (0.011 ml, 0.076 mmol) and mercaptoacetic acid ethyl ester (0.009 ml, 0.076 mmol). The reaction was heated to 50° C. for 14 hours. The reaction mixture was cooled to room temperature and concentrated in vacuo. The resulting tan solid and purified by reverse phase HPLC to afford compound 38A as a white solid (20% yield). MS (APCI+) m/z 1396.4 (M+1) detected.

Example 33

Synthesis of Compound 41

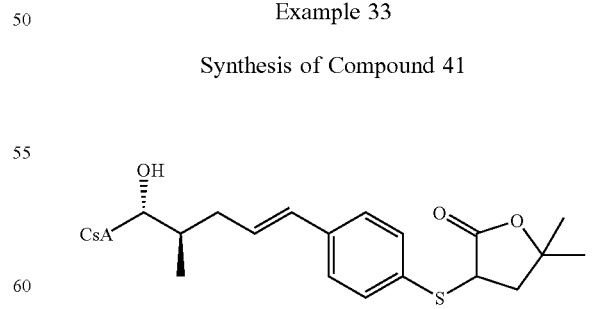

The reaction scheme for the synthesis of compound 41 according to procedure A is shown in FIG. 5.

Step 1: Synthesis of compound 39: To a solution of cyclosporin A (0.820 g, 0.682 mmol) in dichloromethane (1.7 mL) under $N_2$ atmosphere was added thioacetic acid S-(4-vinylphenyl)ester (1.82 g, 10.2 mmol) and Hoveyda's 2$^{nd}$ generation catalyst (43 mg, 0.010 mmol). The resulting green solution was heated to reflux under nitrogen for 16 hours. The reaction mixture was chromatographed on silica eluting with a gradient of dichloromethane, dichloromethane/MeOH (40:1), and dichloromethane/MeOH (20:1) to afford 0.903 g of compound 39 as a gray solid (98% yield). MS (APCI+) m/z 1339 (M+1) detected.

Step 2: Synthesis of compound 40: A solution of compound 39 (0.760 g, 0.568 mmol) in 2:1 THF-MeOH (1.9 mL) was treated with 5.0 N NaOH (0.250 mL, 2.20 equivalents) at room temperature for 4 hours. The reaction was quenched with 5.0 N HCl (0.261 mL, 2.30 equivalents) and diluted with water (10 mL) and ethyl acetate (10 mL). The layers mixture was shaken and separated. The aqueous layer was extracted with an additional 10 mL of ethyl acetate. The combined organics were washed with brine solution, dried with sodium sulfate, filtered, and concentrated in vacuo. Purification on silica gel eluting with 20 to 50% acetone-hexanes provided the desired compound 40 in 55% yield. MS (APCI−) m/z 1295 (M−1) detected.

Step 3: Synthesis of compound 41: Compound 40 (0.025 g, 0.019 mmol) in dichloromethane (0.193 mL, 0.01 M) was treated sequentially with triethylamine (0.008 mL, 3.0 equivalents) and 3-bromo-5,5-dimethydihydrofuran-2-one (0.007 g, 2.0 equiv.) at room temperature. After 19 hours, the reaction was concentrated in vacuo and purified by reverse phase HPLC to afford compound 41 in 11% yield. MS (APCI+) m/z 1409 (M+1) detected.

Example 34

Synthesis of Compound 47

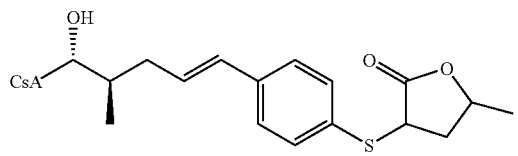

Prepared according to Procedure A, Step 1 from cyclosporin A and 5-methyl-3-(4-vinylphenylsulfanyl)-dihydrofuran-2-one The crude product was chromatographed on silica eluting with a gradient of dichloromethane, dichloromethane/MeOH (97.5:2.5) and dichloromethane/MeOH (95:5). The residue was then purified by reverse phase HPLC to afford compound 47 in 3% yield. MS (APCI+) m/z 1396 (M+1) detected.

Example 35

Synthesis of Compound 48

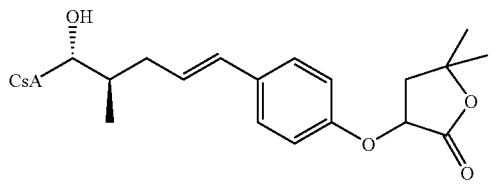

Prepared according to Procedure C, Step 3 from compound 26 (Example 22) and 3-bromo-5,5-dimethydihydrofuran-2-one. The crude product was purified by reverse phase HPLC to afford 36 mg of compound 48 as a white solid (33% yield). MS (ESI+) m/z 1393 (M+1) detected.

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be resorted to falling within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

What is claimed is:

1. A cyclosporin analog having the Formula I

or a pharmaceutically acceptable salt thereof, wherein: residue A has the formula

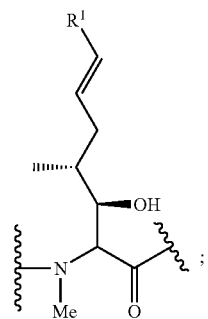

$R^1$ is

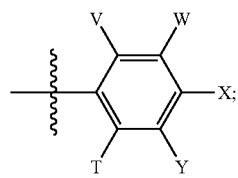

V, W, Y and T are independently selected from H, F, Br, Cl, alkyl, $Z_n$-cycloalkyl, $Z_n$-heterocycloalkyl, $Z_n$-SH, $Z_n$-S-alkyl, $Z_n$-S-heterocycloalkyl, $Z_n$-SA$^r$, $Z_n$-S-$Z_n$R$^5$, —O-$Z_n$-heterocycloalkyl, O-$Z_n$-R$^5$, $Z_n$-OH, $Z_n$-O-alkyl, $Z_n$-O-heterocycloalkyl, $Z_n$-OA$^r$, $Z_n$-NR$^2$R$^3$, $Z_n$-CN, and —O—CHR$^y$C(=O)OR$^x$, wherein said alkyl, cycloalkyl, heterocycloalkyl and A$^r$ portions are optionally substituted with one or more groups independently selected from oxo (provided it is not on said A$^r$), alkyl, F, Cl, Br, O-alkyl, OA$^r$ and $Z_n$C(=O)alkyl;

X is selected from

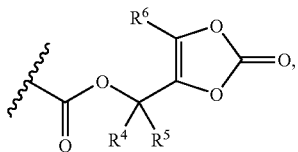

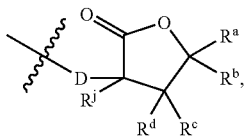

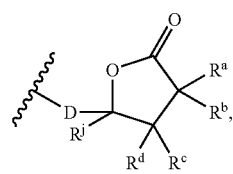

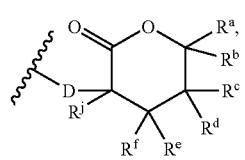

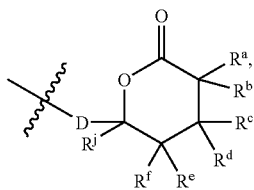

and

D is O, S, —CH$_2$—, —CH$_2$O—, —CH$_2$S—, or —CH$_2$CH$_2$—;

R$^a$, R$^b$, R$^c$, R$^d$, R$^e$, and R$^f$ are independently H, F, Br, Cl, alkyl, Z$_n$-O-alkyl, or Z$_n$-OA$^r$;

R$^j$ is H or alkyl;

R$^x$ is H, alkyl or CH$_2$A$^r$;

R$^y$ is H, alkyl or A$^r$;

R$^2$ and R$^3$ are independently H, alkyl, Z$_n$-A$^r$, or Z$_n$-O-alkyl, wherein said alkyl and A$^r$ portions are optionally substituted with one or more groups independently selected from F, Cl, Br and I;

A$^r$ is a fully unsaturated, a partially unsaturated, or fully saturated carbocyclic or heterocyclic ring, wherein said carbocyclic and heterocyclic rings are optionally substituted with one or more groups independently selected from F, Cl, Br, I, CN, CF$_3$, CHF$_2$, CH$_2$F, OH, O-alkyl, alkoxyaryl, —OC(=O)R$^7$, C(=O)OR$^7$ and —SC(=O)R$^7$;

Z is alkylene having from 1 to 4 carbons, or alkenylene or alkynylene each having from 2 to 4 carbons, wherein said alkylene, alkenylene, and alkynylene are optionally substituted with one or more groups independently selected from alkyl, OH, O-alkyl, NR$^7$R$^8$, and alkyl-NR$^7$R$^8$;

R$^4$, R$^5$ and R$^6$ are independently H, C$_1$–C$_7$ alkyl, alkoxyalkyl, —CO$_2$H or —C(=O)Oalkyl;

R$^7$ and R$^8$ are independently H, alkyl, alkenyl, or alkynyl;

residue B is -αABu-, -Val-, -Thr-, or NVa-;

residue U is -(D)Ala-, (-D)Ser-, —[O-(2-hydroxyethyl)(D)Ser]-, —[O-acyl(D)Ser] or —[O-(2-acyloxyethyl)(D)Ser]-; and n is 0, 1, 2, 3, or 4.

2. The cyclosporin analog of claim 1, wherein residue B is -αAbu- and residue U is -(D)Ala-.

3. The cyclosporin analog of claim 1, where X is

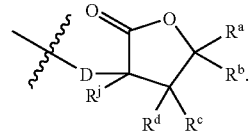

4. The cyclosporin analog of claim 3, wherein D is S.

5. The cyclosporin analog of claim 4, wherein R$^a$ and R$^b$ are independently H or alkyl.

6. The cyclosporin analog of claim 5; wherein R$^1$ is

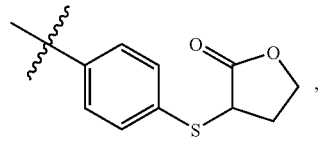

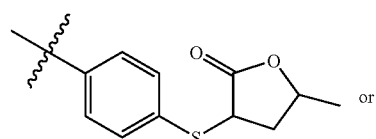

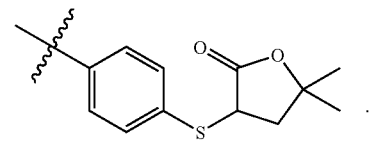

7. The cyclosporin analog of claim 6, wherein residue B is -αAbu- and residue U is -(D)Ala-.

8. The cyclosporin analog of claim 3, wherein D is O.

9. The cyclosporin analog of claim 3, wherein W is F.

10. The cyclosporin analog of claim 8, wherein R$^a$ and R$^b$ are independently H or alkyl.

11. The cyclosporin analog of claim 10, wherein R¹ is

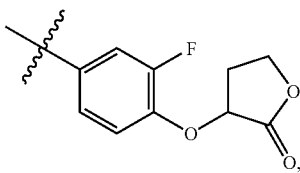

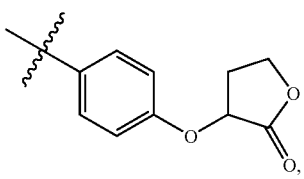

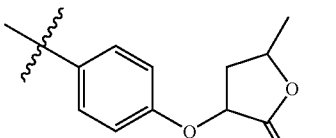, or

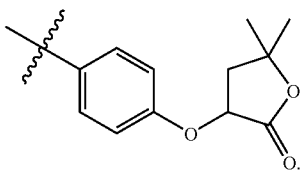

12. The cyclosporin analog of claim 11, wherein residue B is -αAbu- and residue U is -(D)Ala-.

13. The cyclosporin analog of claim 3, wherein D is CH₂.

14. The cyclosporin analog of claim 13, wherein R¹ is

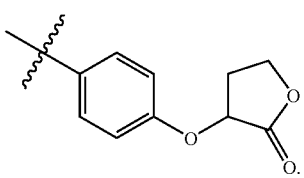

15. The cyclosporin analog of claim 14, wherein residue B is -αAbu- and residue U is -(D)Ala-.

16. The cyclosporin analog of claim 1, wherein X is

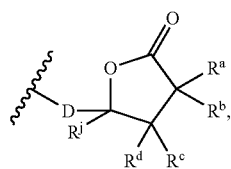

17. The cyclosporin analog of claim 16, wherein D is OCH₂.

18. The cyclosporin analog of claim 17, wherein R¹ is

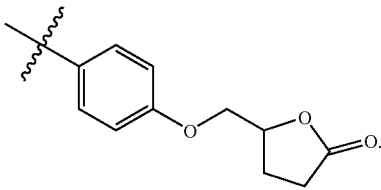

19. The cyclosporin analog of claim 18, wherein residue B is -αAbu- and residue U is -(D)Ala-.

20. The cyclosporin analog of claim 1, wherein X is

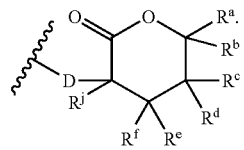

21. The cyclosporin analog of claim 20, wherein D is OCH₂.

22. The cyclosporin analog of claim 1, wherein R¹ is

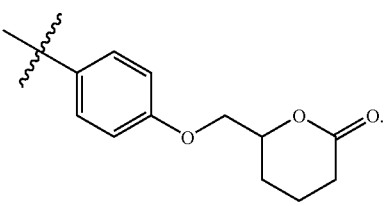

23. The cyclosporin analog of claim 22, wherein residue B is -αAbu- and residue U is -(D)Ala-.

24. A kit for treating an immunoregulatory or respiratory disease, disorder or condition, said kit comprising:
 a) a first pharmaceutical composition comprising a compound of claim 1; and
 b) optionally instructions for use.

25. The kit of claim 24 further comprising (c) a second pharmaceutical composition, wherein the second pharmaceutical composition comprises a second compound for treating an immunoregulatory or respiratory disease, disorder or condition.

26. A method of treating an immunoregulatory or respiratory disease, disorder or condition in a human or animal, comprising administering to said human or animal a compound of claim 1 or a pharmaceutical composition comprising said compound in an amount effective to treat said immunoregulatory or respiratory disease, disorder or condition.

* * * * *